(12) United States Patent
Addonizio et al.

(10) Patent No.: US 8,382,820 B2
(45) Date of Patent: Feb. 26, 2013

(54) STENT HAVING HELICAL ELEMENTS

(75) Inventors: Scott J. Addonizio, Fort Lauderdale, FL (US); David L. Camp, Jr., Hillsboro Beach, FL (US); Gary J. Becker, Miami, FL (US); John D. Pazienza, Pompano Beach, FL (US)

(73) Assignee: OrbusNeich Medical, Inc., Fort Lauderdale, FL (US)

( * ) Notice: Subject to any disclaimer, the term of this patent is extended or adjusted under 35 U.S.C. 154(b) by 0 days.

(21) Appl. No.: 12/178,915

(22) Filed: Jul. 24, 2008

(65) Prior Publication Data

US 2008/0288053 A1     Nov. 20, 2008

Related U.S. Application Data

(63) Continuation of application No. 12/027,382, filed on Feb. 7, 2008, which is a continuation of application No. 10/014,705, filed on Dec. 11, 2001, now Pat. No. 7,329,277, which is a continuation-in-part of application No. 09/511,481, filed on Feb. 23, 2000, (Continued)

(30) Foreign Application Priority Data

Jun. 13, 1997   (EP) ..................................... 97201799
May 6, 1998    (EP) ..................................... 98201446

(51) Int. Cl.
*A61F 2/06*    (2006.01)
(52) U.S. Cl. ...................................................... 623/1.22
(58) Field of Classification Search ................. 623/1.15, 623/1.22
See application file for complete search history.

(56) References Cited

U.S. PATENT DOCUMENTS

| | | |
|---|---|---|
| 3,657,744 A | 4/1972 | Ersek |
| 4,464,722 A | 8/1984 | Von Osten |
| 5,102,417 A | 4/1992 | Palmaz |
| 5,104,404 A | 4/1992 | Wolff |

(Continued)

FOREIGN PATENT DOCUMENTS

| | | |
|---|---|---|
| DE | 29702671 U1 | 5/1997 |
| DE | 19717475 C1 | 9/1998 |

(Continued)

OTHER PUBLICATIONS

Cover Letter Filed to Reexamination Request of U.S. Patent No. 7,967,852.

(Continued)

*Primary Examiner* — David Isabella
*Assistant Examiner* — Ann Schillinger
(74) *Attorney, Agent, or Firm* — Christopher & Weisberg, P.A.

(57) ABSTRACT

An expandable stent comprised of a plurality of helical segments is disclosed. In one embodiment, the stent is generally cylindrical in shape having a cylindrical axis, and comprises a first and second set of helical segments. The helical segments in the first set are substantially parallel and have a first pitch forming a first helical angle with respect to the cylindrical axis. The helical segments in the second set are also generally parallel to each other and form a second pitch that differs from the first pitch, thereby forming a second helical angle with respect to the cylindrical axis. In an alternative embodiment, the stent comprises one set of helical segments and a plurality of circumferential elements that are joined together by the helical segments to form a plurality of cylindrical elements which are joined together to form a stent body. The stent may also have endzones.

11 Claims, 18 Drawing Sheets

Related U.S. Application Data now Pat. No. 7,108,714, which is a continuation of application No. 09/094,402, filed on Jun. 10, 1998, now Pat. No. 6,117,165.

(60) Provisional application No. 60/254,688, filed on Dec. 11, 2000.

(56) References Cited

U.S. PATENT DOCUMENTS

| | | | |
|---|---|---|---|
| 5,133,732 A | 7/1992 | Wiktor | |
| 5,158,548 A | 10/1992 | Lau et al. | |
| 5,217,483 A | 6/1993 | Tower | |
| 5,226,913 A | 7/1993 | Pinchuk | |
| 5,304,200 A | 4/1994 | Spaulding | |
| 5,354,308 A | 10/1994 | Simon et al. | |
| 5,356,423 A | 10/1994 | Tihon et al. | |
| 5,370,683 A * | 12/1994 | Fontaine | 623/1.22 |
| 5,421,955 A | 6/1995 | Lau et al. | |
| 5,443,498 A * | 8/1995 | Fontaine | 623/1.17 |
| 5,449,373 A | 9/1995 | Pinchasik | |
| 5,507,767 A | 4/1996 | Maeda et al. | |
| 5,514,154 A | 5/1996 | Lau et al. | |
| 5,527,354 A | 6/1996 | Fontaine et al. | |
| 5,545,210 A | 8/1996 | Hess et al. | |
| 5,549,663 A * | 8/1996 | Cottone, Jr. | 623/1.22 |
| 5,591,230 A | 1/1997 | Horn et al. | |
| 5,630,829 A | 5/1997 | Lauterjung | |
| 5,667,523 A | 9/1997 | Bynon et al. | |
| 5,697,971 A * | 12/1997 | Fischell et al. | 623/1.15 |
| 5,716,396 A | 2/1998 | Williams, Jr. | |
| 5,725,572 A | 3/1998 | Lam et al. | |
| 5,733,303 A | 3/1998 | Israel et al. | |
| 5,741,327 A | 4/1998 | Frantzen | |
| 5,755,776 A | 5/1998 | Al-Saadon | |
| 5,755,781 A | 5/1998 | Jayaraman | |
| 5,776,161 A | 7/1998 | Globerman | |
| 5,800,521 A | 9/1998 | Orth | |
| 5,810,872 A | 9/1998 | Kanesaka et al. | |
| 5,824,040 A | 10/1998 | Cox | |
| 5,824,043 A | 10/1998 | Cottone, Jr. | |
| 5,843,117 A * | 12/1998 | Alt et al. | 623/1.15 |
| 5,843,120 A | 12/1998 | Israel et al. | |
| 5,843,164 A | 12/1998 | Frantzen et al. | |
| 5,843,175 A | 12/1998 | Frantzen | |
| 5,846,246 A | 12/1998 | Dirks et al. | |
| 5,855,597 A | 1/1999 | Jayaraman | |
| 5,860,999 A | 1/1999 | Schnepp-Pesch et al. | |
| 5,876,449 A | 3/1999 | Starck et al. | |
| 5,879,381 A | 3/1999 | Moriuchi et al. | |
| 5,882,335 A | 3/1999 | Leone et al. | |
| 5,895,406 A * | 4/1999 | Gray et al. | 623/1.15 |
| 5,902,317 A | 5/1999 | Kleshinski et al. | |
| 5,911,754 A | 6/1999 | Kanesaka et al. | |
| 5,913,897 A * | 6/1999 | Corso et al. | 623/1.15 |
| 5,925,061 A | 7/1999 | Ogi | |
| 5,935,161 A | 8/1999 | Robinson et al. | |
| 5,938,697 A | 8/1999 | Killion et al. | |
| 5,948,016 A | 9/1999 | Jang | |
| 5,964,798 A | 10/1999 | Imran | |
| 5,972,018 A | 10/1999 | Israel et al. | |
| 5,980,552 A | 11/1999 | Pinchasik et al. | |
| 6,013,854 A | 1/2000 | Moriuchi | |
| 6,017,365 A | 1/2000 | Von Oepen | |
| 6,019,789 A | 2/2000 | Dinh et al. | |
| 6,033,433 A | 3/2000 | Ehr et al. | |
| 6,042,597 A * | 3/2000 | Kveen et al. | 623/1.15 |
| 6,053,940 A | 4/2000 | Wijay | |
| 6,059,811 A | 5/2000 | Pinchasik et al. | |
| 6,083,259 A | 7/2000 | Frantzen | |
| 6,099,559 A | 8/2000 | Nolting | |
| 6,099,561 A | 8/2000 | Alt | |
| 6,106,548 A | 8/2000 | Roubin et al. | |
| 6,113,627 A * | 9/2000 | Jang | 623/1.5 |
| 6,117,165 A * | 9/2000 | Becker | 623/1.15 |
| 6,123,721 A | 9/2000 | Jang | |
| 6,124,523 A | 9/2000 | Banas | |
| 6,129,755 A | 10/2000 | Mathis et al. | |
| 6,132,460 A | 10/2000 | Thompson | |
| 6,132,461 A * | 10/2000 | Thompson | 623/1.15 |
| 6,136,023 A | 10/2000 | Boyle | |
| 6,171,334 B1 | 1/2001 | Cox | |
| 6,174,326 B1 | 1/2001 | Kitaoka et al. | |
| 6,179,867 B1 | 1/2001 | Cox | |
| 6,190,403 B1 | 2/2001 | Fischell et al. | |
| 6,200,334 B1 | 3/2001 | Jang | |
| 6,200,337 B1 | 3/2001 | Moriuchi et al. | |
| 6,203,569 B1 | 3/2001 | Wijay | |
| 6,231,598 B1 | 5/2001 | Berry et al. | |
| 6,238,409 B1 | 5/2001 | Hojeibane | |
| 6,241,762 B1 | 6/2001 | Shanley | |
| 6,245,101 B1 | 6/2001 | Drasler et al. | |
| 6,254,628 B1 | 7/2001 | Wallace et al. | |
| 6,254,632 B1 | 7/2001 | Wu et al. | |
| 6,261,319 B1 | 7/2001 | Kveen | |
| 6,264,689 B1 | 7/2001 | Colgan et al. | |
| 6,270,524 B1 | 8/2001 | Kim | |
| 6,309,414 B1 | 10/2001 | Rolando et al. | |
| 6,319,277 B1 | 11/2001 | Rudnick et al. | |
| 6,331,188 B1 | 12/2001 | Lau et al. | |
| 6,331,189 B1 | 12/2001 | Wolinsky et al. | |
| 6,340,366 B2 | 1/2002 | Wijay | |
| 6,348,065 B1 | 2/2002 | Brown | |
| 6,350,277 B1 | 2/2002 | Kocur | |
| 6,355,057 B1 | 3/2002 | DeMarais et al. | |
| 6,395,020 B1 | 5/2002 | Ley et al. | |
| 6,398,805 B1 | 6/2002 | Alt | |
| 6,423,091 B1 * | 7/2002 | Hojeibane | 623/1.15 |
| 6,432,132 B1 | 8/2002 | Cottone | |
| 6,443,982 B1 | 9/2002 | Israel et al. | |
| 6,461,381 B2 | 10/2002 | Israel et al. | |
| 6,464,722 B2 | 10/2002 | Israel et al. | |
| 6,485,508 B1 | 11/2002 | McGuinness | |
| 6,506,211 B1 | 1/2003 | Skubitz et al. | |
| 6,508,834 B1 | 1/2003 | Pinchasik et al. | |
| 6,533,809 B2 | 3/2003 | von Oepen | |
| 6,551,350 B1 | 4/2003 | Thornton et al. | |
| 6,569,193 B1 | 5/2003 | Cox et al. | |
| 6,579,314 B1 | 6/2003 | Lombardi et al. | |
| 6,582,461 B1 | 6/2003 | Burmeister et al. | |
| 6,589,276 B2 | 7/2003 | Pinchasik et al. | |
| 6,602,285 B1 | 8/2003 | Von Oepen et al. | |
| 6,610,086 B1 * | 8/2003 | Kock et al. | 623/1.22 |
| 6,620,201 B1 | 9/2003 | Nadal | |
| 6,635,084 B2 | 10/2003 | Israel et al. | |
| 6,652,579 B1 | 11/2003 | Cox | |
| 6,682,554 B2 | 1/2004 | Von Oepen et al. | |
| 6,730,116 B1 | 5/2004 | Wolinsky | |
| 6,730,117 B1 * | 5/2004 | Tseng et al. | 623/1.16 |
| 6,736,844 B1 | 5/2004 | Glatt | |
| 6,776,793 B2 | 8/2004 | Brown et al. | |
| 6,818,014 B2 | 11/2004 | Brown et al. | |
| 6,821,292 B2 * | 11/2004 | Pazienza et al. | 623/1.15 |
| 6,875,228 B2 | 4/2005 | Pinchasik et al. | |
| 6,929,660 B1 | 8/2005 | Ainsworth et al. | |
| 6,974,475 B1 | 12/2005 | Wall | |
| 6,981,986 B1 | 1/2006 | Brown et al. | |
| 7,081,130 B2 * | 7/2006 | Jang | 623/1.17 |
| 7,204,848 B1 | 4/2007 | Brown et al. | |
| 7,329,277 B2 * | 2/2008 | Addonizio et al. | 623/1.22 |
| 7,404,823 B2 | 7/2008 | Gregorich et al. | |
| 7,682,384 B2 * | 3/2010 | Addonizio et al. | 623/1.22 |
| 7,942,922 B2 * | 5/2011 | Addonizio et al. | 623/1.15 |
| 7,967,852 B2 * | 6/2011 | Addonizio et al. | 623/1.15 |
| 2001/0029397 A1 * | 10/2001 | Thompson | 623/1.16 |
| 2001/0056298 A1 | 12/2001 | Brown et al. | |
| 2002/0095206 A1 * | 7/2002 | Addonizio et al. | 623/1.15 |
| 2002/0095208 A1 | 7/2002 | Gregorich et al. | |
| 2002/0116044 A1 | 8/2002 | Cottone et al. | |
| 2003/0225448 A1 | 12/2003 | Gerberding | |
| 2004/0243216 A1 | 12/2004 | Gregorich | |
| 2005/0049687 A1 | 3/2005 | Yang et al. | |
| 2007/0073384 A1 | 3/2007 | Brown et al. | |
| 2008/0065195 A1 | 3/2008 | Brown et al. | |
| 2008/0281406 A1 * | 11/2008 | Addonizio et al. | 623/1.22 |

| | | | | |
|---|---|---|---|---|
| 2008/0281407 | A1* | 11/2008 | Addonizio et al. | 623/1.22 |
| 2008/0288050 | A1* | 11/2008 | Addonizio et al. | 623/1.22 |
| 2008/0288051 | A1* | 11/2008 | Addonizio et al. | 623/1.22 |
| 2008/0288052 | A1* | 11/2008 | Addonizio et al. | 623/1.22 |
| 2008/0288053 | A1* | 11/2008 | Addonizio et al. | 623/1.22 |
| 2008/0294241 | A1* | 11/2008 | Addonizio et al. | 623/1.16 |
| 2008/0294243 | A1* | 11/2008 | Addonizio et al. | 623/1.22 |
| 2008/0294244 | A1* | 11/2008 | Addonizio et al. | 623/1.22 |
| 2008/0319537 | A1* | 12/2008 | Addonizio et al. | 623/1.22 |
| 2009/0024198 | A1* | 1/2009 | Addonizio et al. | 623/1.2 |
| 2009/0024207 | A1* | 1/2009 | Addonizio et al. | 623/1.22 |
| 2010/0211152 | A1* | 8/2010 | Addonizio et al. | 623/1.2 |
| 2010/0324661 | A1* | 12/2010 | Addonizio et al. | 623/1.16 |
| 2010/0324662 | A1* | 12/2010 | Addonizio et al. | 623/1.16 |

FOREIGN PATENT DOCUMENTS

| | | |
|---|---|---|
| EP | 0565251 A1 | 10/1993 |
| EP | 0645125 A1 | 3/1995 |
| EP | 0686379 A2 | 12/1995 |
| EP | 0734698 A2 | 10/1996 |
| EP | 0800800 A1 | 10/1997 |
| EP | 0801934 A2 | 10/1997 |
| EP | 876806 A1 | 11/1998 |
| EP | 0876806 A1 | 11/1998 |
| EP | 0884029 A1 | 12/1998 |
| EP | 0945107 A2 | 9/1999 |
| EP | 945107 A2 | 9/1999 |
| EP | 0968689 A2 | 1/2000 |
| EP | 0970664 A2 | 1/2000 |
| EP | 0983753 A1 | 3/2000 |
| EP | 1008329 A1 | 6/2000 |
| EP | 1025812 A1 | 9/2000 |
| EP | 1123065 B1 | 11/2006 |
| EP | 1852089 A2 | 11/2007 |
| EP | 2204142 A1 | 7/2010 |
| FR | 2758253 A1 | 7/1998 |
| GB | 2281865 A1 | 3/1995 |
| WO | 9417754 A1 | 8/1994 |
| WO | 9526695 A2 | 10/1995 |
| WO | 96/26689 A1 | 9/1996 |
| WO | 9626689 A1 | 9/1996 |
| WO | 97/21399 A1 | 6/1997 |
| WO | 9726840 A1 | 7/1997 |
| WO | 9732544 A1 | 9/1997 |
| WO | 97/40780 A1 | 11/1997 |
| WO | 9820810 A1 | 5/1998 |
| WO | 9830173 A1 | 7/1998 |
| WO | 9840035 A1 | 9/1998 |
| WO | 9856312 A1 | 12/1998 |
| WO | 9912495 A1 | 3/1999 |
| WO | 9939660 A1 | 8/1999 |
| WO | 9949810 A1 | 10/1999 |
| WO | 0013611 A1 | 3/2000 |
| WO | 0030563 A1 | 6/2000 |
| WO | 0045742 A1 | 8/2000 |
| WO | 0071053 A1 | 11/2000 |
| WO | 0158384 A1 | 8/2001 |
| WO | 0189421 A2 | 11/2001 |

OTHER PUBLICATIONS

Power Filed to Reexamination Request of U.S. Patent No. 7,967,852.
Transmittal Filed to Reexamination Request of U.S. Patent No. 7,967,852.
IDS Filed to Reexamination Request of U.S. Patent No. 7,967,852.
Declaration Filed to Reexamination Request of U.S. Patent No. 7,967,852.
Petition Filed to Reexamination Request of U.S. Patent No. 7,967,852.
US7967852 Filed to Reexamination Request of U.S. Patent No. 7,967,852.
IDSAA1 to Reexamination Request of U.S. Patent No. 7,967,852.
IDSAB1 to Reexamination Request of U.S. Patent No. 7,967,852.
IDSAC1 to Reexamination Request of U.S. Patent No. 7,967,852.
IDSAG1 to Reexamination Request of U.S. Patent No. 7,967,852.
IDSAD1 to Reexamination Request of U.S. Patent No. 7,967,852.
IDSAH1 to Reexamination Request of U.S. Patent No. 7,967,852.
IDSAI1 to Reexamination Request of U.S. Patent No. 7,967,852.
IDSAJ1 to Reexamination Request of U.S. Patent No. 7,967,852.
IDSAK1 to Reexamination Request of U.S. Patent No. 7,967,852.
Appendix 47 to Reexamination Request of U.S. Patent No. 7,967,852.
Appendix 48 to Reexamination Request of U.S. Patent No. 7,967,852.
Appendix 49 to Reexamination Request of U.S. Patent No. 7,967,852.
Appendix 50 to Reexamination Request of U.S. Patent No. 7,967,852.
Appendix 51 to Reexamination Request of U.S. Patent No. 7,967,852.
Notice of Opposition dated Jul. 28, 2011 re EP 1341482.
Notice of Opposition dated Aug. 5, 2011 re EP 1341482.
Request for Reexamination of U.S. Patent 7,942,922 Part 1 of 4.
Appendix 1 to Reexamination Request of U.S. Patent 7,942,922.
Appendix 2 to Reexamination Request of U.S. Patent 7,942,922.
Appendix 3 to Reexamination Request of U.S. Patent 7,942,922.
Appendix 4 to Reexamination Request of U.S. Patent 7,942,922.
Appendix 5 to Reexamination Request of U.S. Patent 7,942,922.
Appendix 6 to Reexamination Request of U.S. Patent 7,942,922.
Appendix 7 to Reexamination Request of U.S. Patent 7,942,922.
Appendix 8 to Reexamination Request of U.S. Patent 7,942,922.
Appendix 9 to Reexamination Request of U.S. Patent 7,942,922.
Appendix 10 to Reexamination Request of U.S. Patent 7,942,922.
Appendix 11 to Reexamination Request of U.S. Patent 7,942,922.
Appendix 12 to Reexamination Request of U.S. Patent 7,942,922.
Appendix 13 to Reexamination Request of U.S. Patent 7,942,922.
Appendix 14 to Reexamination Request of U.S. Patent 7,942,922.
Appendix 15 to Reexamination Request of U.S. Patent 7,942,922.
Appendix 16 to Reexamination Request of U.S. Patent 7,942,922.
Appendix 17 to Reexamination Request of U.S. Patent 7,942,922.
Appendix 18 to Reexamination Request of U.S. Patent 7,942,922.
Appendix 19 to Reexamination Request of U.S. Patent 7,942,922.
Appendix 20 to Reexamination Request of U.S. Patent 7,942,922.
Appendix 21 to Reexamination Request of U.S. Patent 7,942,922.
Appendix 22 to Reexamination Request of U.S. Patent 7,942,922.
Appendix 23 to Reexamination Request of U.S. Patent 7,942,922.
Appendix 24 to Reexamination Request of U.S. Patent 7,942,922.
Appendix 25 to Reexamination Request of U.S. Patent 7,942,922.
Appendix 26 to Reexamination Request of U.S. Patent 7,942,922.
Appendix 27 to Reexamination Request of U.S. Patent 7,942,922.
Appendix 28 to Reexamination Request of U.S. Patent 7,942,922.
Appendix 29 to Reexamination Request of U.S. Patent 7,942,922.
Appendix 30 to Reexamination Request of U.S. Patent 7,942,922.
Appendix 31 to Reexamination Request of U.S. Patent 7,942,922.
Appendix 32 to Reexamination Request of U.S. Patent 7,942,922.
Appendix 33 to Reexamination Request of U.S. Patent 7,942,922.
Appendix 34 to Reexamination Request of U.S. Patent 7,942,922.
Appendix 35 to Reexamination Request of U.S. Patent 7,942,922.
Appendix 36 to Reexamination Request of U.S. Patent 7,942,922.
Appendix 37 to Reexamination Request of U.S. Patent 7,942,922.
Appendix 38 to Reexamination Request of U.S. Patent 7,942,922.
Appendix 39 to Reexamination Request of U.S. Patent 7,942,922.
Appendix 40 to Reexamination Request of U.S. Patent 7,942,922.
Appendix 41 to Reexamination Request of U.S. Patent 7,942,922.
Appendix 42 to Reexamination Request of U.S. Patent 7,942,922.
Appendix 43 to Reexamination Request of U.S. Patent 7,942,922.
Appendix 44 to Reexamination Request of U.S. Patent 7,942,922.
Appendix 45 to Reexamination Request of U.S. Patent 7,942,922.
Request for Reexamination of U.S. Patent 7,942,922 Part 2.
Request for Reexamination of U.S. Patent 7,942,922 Part 3.
Request for Reexamination of U.S. Patent 7,942,922 Part 4.
Cover Letter Filed to Reexamination Request of U.S. Patent 7,942,922.
Power Filed to Reexamination Request of U.S. Patent 7,942,922.
Transmittal Filed to Reexamination Request of U.S. Patent 7,942,922.
IDS Filed to Reexamination Request of U.S. Patent 7,942,922.
Declaration Filed to Reexamination Request of U.S. Patent 7,942,922.
Petition Filed to Reexamination Request of U.S. Patent 7,942,922.

US7942922 Filed to Reexamination Request of U.S. Patent 7,942,922.
IDSAA1 to Reexamination Request of U.S. Patent 7,942,922.
IDSAB1 to Reexamination Request of U.S. Patent 7,942,922.
IDSAC1 to Reexamination Request of U.S. Patent 7,942,922.
IDSAG1 to Reexamination Request of U.S. Patent 7,942,922.
IDSAD1 to Reexamination Request of U.S. Patent 7,942,922.
IDSAH1 to Reexamination Request of U.S. Patent 7,942,922.
IDSAI1 to Reexamination Request of U.S. Patent 7,942,922.
IDSAJ1 to Reexamination Request of U.S. Patent 7,942,922.
Request for Reexamination of U.S. Patent 7,967,852 Part 1 of 4.
Appendix 1 to Reexamination Request of U.S. Patent 7,967,852.
Appendix 2 to Reexamination Request of U.S. Patent 7,967,852.
Appendix 3 to Reexamination Request of U.S. Patent 7,967,852.
Appendix 4 to Reexamination Request of U.S. Patent 7,967,852.
Appendix 5 to Reexamination Request of U.S. Patent 7,967,852.
Appendix 6 to Reexamination Request of U.S. Patent 7,967,852.
Appendix 7 to Reexamination Request of U.S. Patent 7,967,852.
Appendix 8 to Reexamination Request of U.S. Patent 7,967,852.
Appendix 9 to Reexamination Request of U.S. Patent 7,967,852.
Appendix 10 to Reexamination Request of U.S. Patent 7,967,852.
Appendix 11 to Reexamination Request of U.S. Patent 7,967,852.
Appendix 12 to Reexamination Request of U.S. Patent 7,967,852.
Appendix 13 to Reexamination Request of U.S. Patent 7,967,852.
Appendix 14 to Reexamination Request of U.S. Patent 7,967,852.
Appendix 15 to Reexamination Request of U.S. Patent 7,967,852.
Appendix 16 to Reexamination Request of U.S. Patent 7,967,852.
Appendix 17 to Reexamination Request of U.S. Patent 7,967,852.
Appendix 18 to Reexamination Request of U.S. Patent 7,967,852.
Appendix 19 to Reexamination Request of U.S. Patent 7,967,852.
Appendix 20 to Reexamination Request of U.S. Patent 7,967,852.
Appendix 21 to Reexamination Request of U.S. Patent 7,967,852.
Appendix 22 to Reexamination Request of U.S. Patent 7,967,852.
Appendix 23 to Reexamination Request of U.S. Patent 7,967,852.
Appendix 24 to Reexamination Request of U.S. Patent 7,967,852.
Appendix 25 to Reexamination Request of U.S. Patent 7,967,852.
Appendix 26 to Reexamination Request of U.S. Patent 7,967,852.
Appendix 27 to Reexamination Request of U.S. Patent 7,967,852.
Appendix 28 to Reexamination Request of U.S. Patent 7,967,852.
Appendix 29 to Reexamination Request of U.S. Patent 7,967,852.
Appendix 30 to Reexamination Request of U.S. Patent 7,967,852.
Appendix 31 to Reexamination Request of U.S. Patent 7,967,852.
Appendix 32 to Reexamination Request of U.S. Patent 7,967,852.
Appendix 33 to Reexamination Request of U.S. Patent 7,967,852.
Appendix 34 to Reexamination Request of U.S. Patent 7,967,852.
Appendix 35 to Reexamination Request of U.S. Patent 7,967,852.
Appendix 36 to Reexamination Request of U.S. Patent 7,967,852.
Appendix 37 to Reexamination Request of U.S. Patent 7,967,852.
Appendix 38 to Reexamination Request of U.S. Patent 7,967,852.
Appendix 39 to Reexamination Request of U.S. Patent 7,967,852.
Appendix 40 to Reexamination Request of U.S. Patent 7,967,852.
Appendix 41 to Reexamination Request of U.S. Patent 7,967,852.
Appendix 42 to Reexamination Request of U.S. Patent 7,967,852.
Appendix 43 to Reexamination Request of U.S. Patent 7,967,852.
Appendix 44 to Reexamination Request of U.S. Patent 7,967,852.
Appendix 45 to Reexamination Request of U.S. Patent 7,967,852.
Appendix 46 to Reexamination Request of U.S. Patent 7,967,852.
Request for Reexamination of U.S. Patent 7,967,852 Part 2.
Request for Reexamination of U.S. Patent 7,967,852 Part 3.
Request for Reexamination of U.S. Patent 7,967,852 Part 4.
Order Granting Re-Exam request for USP 7,967,852.
Re-Exam Office Action for USP 7,967,852.
Order Granting Re-Exam request for USP 7,942,922.
Re-Exam Office Action for USP 7,942,922.
Reexamination Request of U.S. Patent 7,329,277—Appendix 1.
Reexamination Request of U.S. Patent 7,329,277—Appendix 2.
Reexamination Request of U.S. Patent 7,329,277—Appendix 3.
Reexamination Request of U.S. Patent 7,329,277—Appendix 4.
Reexamination Request of U.S. Patent 7,329,277—Appendix 5.
Reexamination Request of U.S. Patent 7,329,277—Appendix 6.
Reexamination Request of U.S. Patent 7,329,277—Appendix 7.
Reexamination Request of U.S. Patent 7,329,277—Appendix 8.
Reexamination Request of U.S. Patent 7,329,277—Appendix 9.
Reexamination Request of U.S. Patent 7,329,277—Appendix 10.
Reexamination Request of U.S. Patent 7,329,277—Appendix 11.
Reexamination Request of U.S. Patent 7,329,277—Appendix 12.
Reexamination Request of U.S. Patent 7,329,277—Appendix 13.
Reexamination Request of U.S. Patent 7,329,277—Appendix 14.
Reexamination Request of U.S. Patent 7,329,277—Appendix 15.
Reexamination Request of U.S. Patent 7,329,277—Appendix 16.
Reexamination Request of U.S. Patent 7,329,277—Appendix 17.
Reexamination Request of U.S. Patent 7,329,277—Appendix 18.
Reexamination Request of U.S. Patent 7,329,277—Appendix 19.
Reexamination Request of U.S. Patent 7,329,277—Appendix 20.
Reexamination Request of U.S. Patent 7,329,277—Appendix 21.
Reexamination Request of U.S. Patent 7,329,277—Appendix 22.
Reexamination Request of U.S. Patent 7,329,277—Appendix 23.
Reexamination Request of U.S. Patent 7,329,277—Appendix 24.
Reexamination Request of U.S. Patent 7,329,277—Appendix 25.
Reexamination Request of U.S. Patent 7,329,277—Appendix 26.
Reexamination Request of U.S. Patent 7,329,277—Appendix 27.
Reexamination Request of U.S. Patent 7,329,277—Appendix 28.
Reexamination Request of U.S. Patent 7,329,277—Appendix 29.
Reexamination Request of U.S. Patent 7,329,277—Appendix 30.
Reexamination Request of U.S. Patent 7,329,277—Appendix 31.
Reexamination Request of U.S. Patent 7,329,277—Appendix 32.
Reexamination Request of U.S. Patent 7,329,277—Appendix 33.
Reexamination Request of U.S. Patent 7,329,277—Appendix 34.
Reexamination Request of U.S. Patent 7,329,277—Appendix 35.
Reexamination Request of U.S. Patent 7,329,277—Appendix 36.
Reexamination Request of U.S. Patent 7,329,277—Appendix 37.
Reexamination Request of U.S. Patent 7,329,277—Appendix 38.
Reexamination Request of U.S. Patent 7,329,277—Appendix 39.
Reexamination Request of U.S. Patent 7,329,277—Appendix 40.
Reexamination Request of U.S. Patent 7,329,277—Appendix 41.
Reexamination Request of U.S. Patent 7,329,277—Declaration.
Reexamination Request of U.S. Patent 7,329,277—Information Disclosure Statement.
Reexamination Request of U.S. Patent 7,329,277—Power of Attorney.
Reexamination Request of U.S. Patent 7,329,277—PTO1449.
Reexamination Request of U.S. Patent 7,329,277—Part 1.
Reexamination Request of U.S. Patent 7,329,277—Part 2.
Reexamination Request of U.S. Patent 7,329,277—Transmittal Letter.
Reexamination Request of U.S. Patent 7,329,277—Appendix 42.
Reexamination Request of U.S. Patent 7,329,277—Appendix 43.
Reexamination Request of U.S. Patent 7,329,277—Appendix 44.
Reexamination Request of U.S. Patent 7,329,277—Appendix 45.
Reexamination Request of U.S. Patent 7,329,277—Appendix 46.
Reexamination Request of U.S. Patent 7,329,277—Appendix 47.
Reexamination Request of U.S. Patent 7,329,277—Appendix 48.
Reexamination Request of U.S. Patent 7,329,277—Appendix 49.
Reexamination Request of U.S. Patent 7,329,277—Appendix 50.
Reexamination Request of U.S. Patent 7,329,277—Appendix 51.
Reexamination Request of U.S. Patent 7,329,277—Appendix 52.
Reexamination Request of U.S. Patent 7,329,277—Appendix 53.
Reexamination Request of U.S. Patent 7,329,277—Appendix 54.
Reexamination Request of U.S. Patent 7,329,277—Appendix 55.
Reexamination Request of U.S. Patent 7,329,277—Appendix 56.
Reexamination Request of U.S. Patent 7,329,277—Appendix 57.
Reexamination Request of U.S. Patent 7,329,277—Appendix 58.
Reexamination Request of U.S. Patent 7,329,277—Appendix 59.
Reexamination Request of U.S. Patent 7,329,277—Appendix 60.
Reexamination Request of U.S. Patent 7,329,277—Appendix 61.
Reexamination Request of U.S. Patent 7,329,277—Appendix 62.
Reexamination Request of U.S. Patent 7,329,277—Appendix 63.
Reexamination Request of U.S. Patent 7,329,277—Appendix 64.
Reexamination Request of U.S. Patent 7,329,277—Appendix 65.
Reexamination Request of U.S. Patent 7,329,277—Appendix 66.
Reexamination Request of U.S. Patent 7,329,277—Appendix 67.
Reexamination Request of U.S. Patent 7,329,277—Appendix 68.
Reexamination Request of U.S. Patent 6,821,292—Appendix 1.
Reexamination Request of U.S. Patent 6,821,292—Appendix 2.
Reexamination Request of U.S. Patent 6,821,292—Appendix 3.
Reexamination Request of U.S. Patent 6,821,292—Appendix 4.

Reexamination Request of U.S. Patent 6,821,292—Appendix 5.
Reexamination Request of U.S. Patent 6,821,292—Appendix 6.
Reexamination Request of U.S. Patent 6,821,292—Appendix 7.
Reexamination Request of U.S. Patent 6,821,292—Appendix 8.
Reexamination Request of U.S. Patent 6,821,292—Appendix 9.
Reexamination Request of U.S. Patent 6,821,292—Appendix 10.
Reexamination Request of U.S. Patent 6,821,292—Appendix 11.
Reexamination Request of U.S. Patent 6,821,292—Appendix 12.
Reexamination Request of U.S. Patent 6,821,292—Appendix 13.
Reexamination Request of U.S. Patent 6,821,292—Appendix 14.
Reexamination Request of U.S. Patent 6,821,292—Appendix 15.
Reexamination Request of U.S. Patent 6,821,292—Appendix 16.
Reexamination Request of U.S. Patent 6,821,292—Appendix 17.
Reexamination Request of U.S. Patent 6,821,292—Appendix 18.
Reexamination Request of U.S. Patent 6,821,292—Appendix 19.
Reexamination Request of U.S. Patent 6,821,292—Appendix 20.
Reexamination Request of U.S. Patent 6,821,292—Appendix 21.
Reexamination Request of U.S. Patent 6,821,292—Appendix 22.
Reexamination Request of U.S. Patent 6,821,292—Appendix 23.
Reexamination Request of U.S. Patent 6,821,292—Appendix 24.
Reexamination Request of U.S. Patent 6,821,292—Appendix 25.
Reexamination Request of U.S. Patent 6,821,292—Appendix 26.
Reexamination Request of U.S. Patent 6,821,292—Appendix 27.
Reexamination Request of U.S. Patent 6,821,292—Appendix 28.
Reexamination Request of U.S. Patent 6,821,292—Appendix 29.
Reexamination Request of U.S. Patent 6,821,292—Appendix 30.
Reexamination Request of U.S. Patent 6,821,292—Appendix 31.
Reexamination Request of U.S. Patent 6,821,292—Appendix 32.
Reexamination Request of U.S. Patent 6,821,292—Appendix 33.
Reexamination Request of U.S. Patent 6,821,292—Appendix 34.
Reexamination Request of U.S. Patent 6,821,292—Appendix 35.
Reexamination Request of U.S. Patent 6,821,292—Appendix 36.
Reexamination Request of U.S. Patent 6,821,292—Appendix 37.
Reexamination Request of U.S. Patent 6,821,292—Appendix 38.
Reexamination Request of U.S. Patent 6,821,292—Appendix 39.
Reexamination Request of U.S. Patent 6,821,292—PTO1449.
Reexamination Request of U.S. Patent 6,821,292—Cover Letter.
Reexamination Request of U.S. Patent 6,821,292—Declaration.
Reexamination Request of U.S. Patent 6,821,292—InformationDisclosure Statement.
Reexamination Request of U.S. Patent 6,821,292—Power of Attorney.
Reexamination Request of U.S. Patent 6,821,292—Transmittal Letter.
Reexamination Request of U.S. Patent 6,821,292.
Reexamination Request of U.S. Patent 7,682,384—Appendix 44.
Reexamination Request of U.S. Patent 7,682,384—Appendix 45.
Reexamination Request of U.S. Patent 7,682,384—Appendix 46.
Reexamination Request of U.S. Patent 7,682,384—Appendix 47.
Reexamination Request of U.S. Patent 7,682,384—Appendix 48.
Reexamination Request of U.S. Patent 7,682,384—Appendix 49.
Reexamination Request of U.S. Patent 7,682,384—Appendix 50.
Reexamination Request of U.S. Patent 7,682,384—Appendix 51.
Reexamination Request of U.S. Patent 7,682,384—Appendix 52.
Reexamination Request of U.S. Patent 7,682,384—Appendix 53.
Reexamination Request of U.S. Patent 7,682,384—Appendix 54.
Reexamination Request of U.S. Patent 7,682,384—Appendix 55.
Reexamination Request of U.S. Patent 7,682,384—Taylor Declaration.
Reexamination Request of U.S. Patent 7,682,384—U.S. Appl. No. 60/254,688, filed Dec. 11, 2000.
Reexamination Request of U.S. Patent 7,682,384—PTO1449.
Reexamination Request of U.S. Patent 7,682,384—Cover Letter.
Reexamination Request of U.S. Patent 7,682,384—Information Disclosure Statement.
Reexamination Request of U.S. Patent 7,682,384—Power of Attorney.
Reexamination Request of U.S. Patent 7,682,384—Part 1.
Reexamination Request of U.S. Patent 7,682,384—Part 2.
Reexamination Request of U.S. Patent 7,682,384—Transmittal Letter.
Reexamination Request of U.S. Patent 7,682,384—Appendix 1.
Reexamination Request of U.S. Patent 7,682,384—Appendix 2.
Reexamination Request of U.S. Patent 7,682,384—Appendix 3.
Reexamination Request of U.S. Patent 7,682,384—Appendix 4.
Reexamination Request of U.S. Patent 7,682,384—Appendix 5.
Reexamination Request of U.S. Patent 7,682,384—Appendix 6.
Reexamination Request of U.S. Patent 7,682,384—Appendix 7.
Reexamination Request of U.S. Patent 7,682,384—Appendix 8.
Reexamination Request of U.S. Patent 7,682,384—Appendix 9.
Reexamination Request of U.S. Patent 7,682,384—Appendix 10.
Reexamination Request of U.S. Patent 7,682,384—Appendix 11.
Reexamination Request of U.S. Patent 7,682,384—Appendix 12.
Reexamination Request of U.S. Patent 7,682,384—Appendix 13.
Reexamination Request of U.S. Patent 7,682,384—Appendix 14.
Reexamination Request of U.S. Patent 7,682,384—Appendix 15.
Reexamination Request of U.S. Patent 7,682,384—Appendix 16.
Reexamination Request of U.S. Patent 7,682,384—Appendix 17.
Reexamination Request of U.S. Patent 7,682,384—Appendix 18.
Reexamination Request of U.S. Patent 7,682,384—Appendix 19.
Reexamination Request of U.S. Patent 7,682,384—Appendix 20.
Reexamination Request of U.S. Patent 7,682,384—Appendix 21.
Reexamination Request of U.S. Patent 7,682,384—Appendix 22.
Reexamination Request of U.S. Patent 7,682,384—Appendix 23.
Reexamination Request of U.S. Patent 7,682,384—Appendix 24.
Reexamination Request of U.S. Patent 7,682,384—Appendix 25.
Reexamination Request of U.S. Patent 7,682,384—Appendix 26.
Reexamination Request of U.S. Patent 7,682,384—Appendix 27.
Reexamination Request of U.S. Patent 7,682,384—Appendix 28.
Reexamination Request of U.S. Patent 7,682,384—Appendix 29.
Reexamination Request of U.S. Patent 7,682,384—Appendix 30.
Reexamination Request of U.S. Patent 7,682,384—Appendix 31.
Reexamination Request of U.S. Patent 7,682,384—Appendix 32.
Reexamination Request of U.S. Patent 7,682,384—Appendix 33.
Reexamination Request of U.S. Patent 7,682,384—Appendix 34.
Reexamination Request of U.S. Patent 7,682,384—Appendix 35.
Reexamination Request of U.S. Patent 7,682,384—Appendix 36.
Reexamination Request of U.S. Patent 7,682,384—Appendix 37.
Reexamination Request of U.S. Patent 7,682,384—Appendix 38.
Reexamination Request of U.S. Patent 7,682,384—Appendix 39.
Reexamination Request of U.S. Patent 7,682,384—Appendix 40.
Reexamination Request of U.S. Patent 7,682,384—Appendix 41.
Reexamination Request of U.S. Patent 7,682,384—Appendix 42.
Reexamination Request of U.S. Patent 7,682,384—Appendix 43.
Order Granting Request for Inter Parties Reexamination for U.S. Patent No. 7,682,384.
Office Action for U..S. Patent No. 7,682,384.
Order Granting Request for Inter Parties Reexamination for U.S. Patent No. 7,329,277.
Office Action for U.S. Patent No. 7,329,277.
Order Granting Request for Inter Parties Reexamination for U.S. Patent No. 6,821,292.
Office Action for U.S. Patent No. 6,821,292.
Simon H. Stertzer et al., AVE GFX STENT, Handbook of Coronary Stents, Second Edition, 1997, pp. 45-54, Martin Dunitz Ltd., The Livery House, London, United Kingdom.
Richard A. Schatz et al., Handbook of Coronary Stents, 1997, p. 24, Martin Dunitz Ltd., The Livery House, London, United Kingdom.
Arterial Vascular Engineering Announces Next Generation Stent Launch, http://www.thefreelibrary.com/Arterial+Vascular+Engineering+Announces+Next+Generation+Stent+Launch-a018658409, 2-pages.
Home Medical Devices Products and Medical Procedures Device Approvals and Clearances, Medical Devices, Dec. 1997 PMA Approvals, http://www.fda.gov/medicaldevices/productsandmedicalprocedures/deviceapprovalsandclearances/pmaaprovals/ucm115816.htm, 5-pages.
AVE Commences U.S. Clinical Trial of gfx(TM) Coronary Stent System, http://www.thefreelibrary.com/AVE+Commences+U.S.+Clinical+Trial+of+gfx(TM)+Coronary+Stent+System-a019453153, 4-pages.
Jean Gregoire et al., Handbook of Coronary Stents, 1997, p. 72, Martin Dunitz Ltd., The Livery House, London, United Kingdom.

* cited by examiner

STENT HAVING HELICAL ELEMENTS

CROSS-REFERENCE TO RELATED APPLICATION

This application is a continuation of U.S. patent application Ser. No. 12/027,382, filed on Feb. 7, 2008, which application is a continuation of U.S. patent application Ser. No. 10/014,705, filed on Dec. 11, 2001, now issued U.S. Pat. No. 7,329,277, which application claims the benefit of U.S. Provisional Application No. 60/254,688, filed on Dec. 11, 2000, all of which are hereby incorporated in their entirety by reference. U.S. patent application Ser. No. 10/014,705 is also continuation-in-part of U.S. patent application Ser. No. 09/511,481, filed on Feb. 23, 2000, now U.S. Pat. No. 7,108,714, which is a continuation of U.S. patent application Ser. No. 09/094,402, filed Jun. 10, 1998, now U.S. Pat. No. 6,117,165, all of which are hereby incorporated in their entirety by reference.

FIELD OF THE INVENTION

The present invention relates to prosthetic stents. In particular, the present invention relates to stents having helical elements and to methods for manufacturing the stents of the present invention.

BACKGROUND OF THE INVENTION

Stents are prosthetic devices that are implanted in the lumen of a vessel inside the body to provide support for the vessel's wall. Structural support from stents is particularly important in angioplasty procedures. Typically, stents are implanted within a vessel system to reinforce vessels that are partially occluded, collapsing, weakened, or abnormally dilated. More generally, stents can be used inside any physiological conduit or duct including, for example, arteries, veins, bile ducts, the urinary tract, alimentary tracts, the tracheobronchial tree, a cerebral aqueduct or the genitourinary system. Stents may be used in both humans and animals.

There are typically two types of stents: self expanding stents and balloon expandable stents. Self expanding stents automatically expand once they are released and assume a deployed, expanded state. A balloon expandable stent is expanded using an inflatable balloon catheter. The balloon is inflated to plastically deform the stent. Balloon expandable stents may be implanted by mounting the stent in an unexpanded or crimped state on a balloon segment of a catheter. The catheter, after having the crimped stent placed thereon, is inserted through a puncture in a vessel wall and moved through the vessel until it is positioned in the portion of the vessel that is in need of repair. The stent is then expanded by inflating the balloon catheter against the inside wall of the vessel. Specifically, the stent is plastically deformed by inflating the balloon so that the diameter of the stent is increased and remains at an increased state. In some situations, the vessel in which the stent is implanted may be dilated by the stent itself when the stent is expanded.

The Palmaz-Schatz™ stent, which is disclosed in the Handbook of Coronary Stents by Patrick W. Serruys et al. (Martin Dunitz, LTD 1998), is an example of a balloon expandable stent that had been implanted in hundreds of thousands of patients. The Palmaz-Schatz™ stent, like other known stents, has certain limitations. These include, but are not limited to: (i) low stent-to-vessel ratio uniformity, (ii) comparative rigidity of the stent in a crimped as well as deployed state, and (iii) limited flexibility making delivery and placement in narrow vessels difficult. Stent-to-vessel ratio generally refers to the degree that the vessel wall is supported by the stent in its expanded state and preferably should be uniform throughout the length of the stent. Furthermore because the Palmaz-Schatz™ stent consists of one or more bridges that connect a number of consecutively slotted tubes, there are a number of bare areas in the vessel after the expansion of the stent. These shortfalls are common to many stents. Id. at 36.

SUMMARY OF THE INVENTION

The present invention is directed to expandable stents that have relatively uniform stent-to-vessel ratios when expanded and other desirable properties, as well as methods for making these stents.

An expandable intraluminal endoprosthesis of this kind is characterized in that at least in said first unexpanded state at least a part of said wall of said tubular member comprises a substantially continuous structure of mutually staggered undulations which has been separated from a tube wall, in that said substantially continuous structure comprises at least one pattern which advances substantially helically along a longitudinal axis of said tubular body and in that said structure comprises connection elements connecting adjacent undulations, which connection elements are an integral extension of the undulations which they connected.

The structure making up the wall of the tubular member may be separated from a hollow tube by means of for instance laser cutting or a similar technique available to a skilled person. In this manner a substantially stress-free structure may be created incorporating a substantially helically advancing pattern which can be highly uniform and flexible throughout the length of the device but still facilitates unimpaired design freedom to tailor the pattern to meet additional functionality and to remove specific drawbacks. Moreover as the connecting elements are likewise separated from the tube as the rest of the structure and consequently are entirely integral with said structure the drawbacks associated with the welds in the prior art device may be avoided. The substantial helical pattern within the structure may be designed to form, upon deployment, a substantially continuously advancing spine as a kind of backbone of the device.

A specific embodiment of the endoprosthesis according to the invention is characterized in that said structure comprises a continuous filament which is separated from a tube wall, in that said adjacent undulations are staggered in a substantially helical configuration advancing along a longitudinal axis of the tubular body to form one of said at least one substantially helical pattern within said structure, and in that a first helical turn of said filament around said longitudinal axis of said tubular member is connected to an adjacent second such turn of said filament by means of at least one of said connection elements, being an integral extension of said filament. This embodiment to a large extent compares to the Cordis Coronary Stent referred to above, without however sharing the above described drawbacks of that device.

In order to improve on flexibility in a compressed as well as in a deployed state of the device a further specific embodiment of the endoprosthesis is according to the invention characterized in that adjacent turns of said filament are connected to one another by means of a number of connection elements less than the number of undulations in said turns. Due to the fairly unlimited design freedom in the device of the invention, the number of interconnections between adjacent turns may be adapted freely to suit the flexibility of the device. The less connection between adjacent turns, the more flexible the device will be. Said design freedom moreover allows a variation of the number of interconnections between adjacent turns within the same device to suit an optimal behaviour.

In a preferred embodiment an endoprosthesis is according to the invention characterized in that said structure comprises a number of turns of said filament whereby the connection elements to subsequent turns are radially shifted to form at least one further substantially helical pattern of said at least one substantial helical pattern within said structure. In this manner a kind of primary framework structure may be obtained which supports the vessel wall while maintaining deployed flexibility. More specifically a preferred embodiment of the endoprosthesis according to the invention is characterized in that at least a portion of the structure comprises a number of connection elements which are substantially equally divided in each turn of said filament and in that connection elements in successive turns are helically shifted by approximately one undulation pitch distance. By shifting the connection elements substantially a full pitch distance a structure is realized in which successive connection elements are linked to each other by substantially a full undulation of said first pattern. This undulation introduces significant slack and expandable diameter within the helical spine created by the interlinked connection elements which allows a very gradual expansion of the device transverse to its longitudinal direction. This reduces so-called foreshortening which is a longitudinal shrinking of the device as it is expanded and would otherwise limit the effective range of the device.

A further specific embodiment of the device according to the invention is characterized in that at least some of the connection elements comprise a strut diagonally interconnecting a first side of a first adjoining undulation to an opposite side of a second adjoining undulation, the strut being entirely integral with said adjoining undulations and having a direction different to the helical direction of said one substantial helical pattern within said structure. Upon deployment, this structure, will create a kind of spine which runs over a series of connection elements in a different, or even contra, helical direction compared to that of said one substantially helical pattern. Such multiple-helix structure is capable of providing a significant hoop strength whilst still being flexible and conformal to the natural vessel wall.

In a still further embodiment an endoprosthesis is according to the invention characterized in that the connection elements to subsequent turns are radially shifted by approximately one undulation pitch distance. Due to this regular pattern of connection elements one or more continuous, helically turning spines will be obtained in the deployed state of the device, formed by subsequent struts and the respective sides of the undulations they interconnect. These spines may form a scaffolding lattice which uniformly supports the vessel wall while maintaining deployed flexibility in order to be as conformal as possible with the natural form of the vessel concerned. It has been found that especially lack of the latter, resulting in unnatural straightening of the vessel over a certain length, is a primary cause for late term restenosis of the stented segment. Due to the deployed flexibility and its highly conformal deployed shape this still further embodiment of the invention aims to avoid this problem.

To further improve on flexibility while maintaining hoop strength, i.e. the ability to withstand inwardly directed radial forces, a further specific embodiment of the endoprosthesis according to the invention is characterized in that the first side of said first undulation, said opposite side of said second undulation and said strut have a first filament width and in that the opposite side of said first undulation and the first side of the second undulation have a second filament width, the first filament width being larger than the second filament width. The inventor has recognized that said second filament width may be made smaller than said first filament width, thus gaining flexibility, without deteriorating the strength of the device and particularly its radial hoop strength.

In a further specific embodiment the endoprosthesis according to the invention is characterized in that said strut connecting opposite sides of adjoining undulations of subsequent turns have a substantially S-shaped structure. Such a double curved structure of the connection elements creates more slack between mutually interconnected undulations allowing more expansion as well as an improved stent to vessel ratio at said area once the prosthesis has been deployed.

A still further preferred embodiment of the endoprosthesis according to the invention is characterized in that the connection elements each comprise two intersecting struts which are entirely integral with each other and with the adjoining undulations which they connect. The inventor has recognized that on deployment of the device such an interconnection element will first rotate around its central axis before the entire force applied pulls axially on the point of intersection. As a consequence a certain stress relief is incorporated in the device which allows for a smaller filament width. This does not only add to the flexibility of the device but also leads to a more favourable radio-opacity. Moreover, the intersecting struts leave a substantially unchanged scaffolding area or footprint upon deployment of the structure thereby improving on the eventual stent-to-vessel ratio of the device compared to a connection element which will almost entirely stretch upon deployment.

The design freedom gained by the endoprosthesis according to the invention appears fairly unlimited and can be applied to precisely tailor the properties of the device to specific requirements. Not only the form, number and the location of connection elements but also the filament width and form of particular parts may be adapted in this sense. As an example, a further specific embodiment of the invention is characterized in that the undulations in said filament have a first mutual pitch in a first of said turns of said filament and a second mutual pitch in a second of said turns, the first and second pitch being different from each other. Varying the mutual pitch of the undulations will generally give rise to more or less flexibility in combination with less or more vessel support at the zones concerned.

A still further embodiment of the endoprosthesis according to the invention is characterized in that at least a part of at least one undulation in at least one turn of said at least one substantially helical pattern has an increased amplitude, while at least the adjoining part of an adjoining undulation in an adjacent turn has a correspondingly decreased amplitude. In this case the mechanical properties of the device and especially the manner of deployment as well as the stent-to-vessel ratio may be tailored by offsetting the point where adjacent undulations meet.

More specifically a further embodiment of the endoprosthesis according to the invention is characterized in that a first pair of adjacent undulations of said structure is connected by means of a first connection element, in that a second pair of adjacent undulation of said structure is connected by means of a second connection element, in that in between said first and second pair of connection elements at least one undulation of an intermediate pair of undulations has an increased amplitude, to bridge at least part of the length of said first and second connection element. In this case the inevitable length of the connection elements between adjacent turns of the device is at least partly compensated by the increased amplitude of said at least one undulation, leading to a more uniform deployed stent-to-vessel ratio.

Besides, or even instead of, being formed by a series of substantially helically staggered undulations, a substantially helically advancing pattern within the structure may also be created by the connection elements in themselves. In this respect, a specific embodiment of the endoprosthesis according to the invention is characterized in that said structure comprises at least one series of connection elements which are substantially regularly distributed over at least part of the length of said tubular body and in that successive connection elements within said at least one series are radially shifted to form one substantially helical pattern within said structure. More specifically, a preferred embodiment of the endoprosthesis according to the invention is characterized in that said successive connection elements are mutually connected by an elongated member which has a greater length than the linear distance between said connection elements in said first unexpanded state of the structure, in order to impart radial expandability to the structure.

In this manner a helically advancing spine is realised throughout at least a part of the device which adds to the scaffolding lattice of the structure, especially in the deployed state of the device. One or even more of such spines may give the device a considerable hoop-strength and supporting capability, without depriving the structure of its crimped as well as deployed flexibility. The greater length of the elongated member adds expandable diameter to the individually connected connection elements, imparting additional slack within the structure, an improved expandability and less fore-shortening on the device. This additional circumference allows for side branch access greater than the maximum expanded diameter of the stent along the longitudinal axis. In this respect, a specific embodiment of the endoprosthesis is characterized in that said elongated member comprises a substantially S-curved bent. The S-curved members are situated along the spiral helix equidistantly spaced, along the longitudinal axis of the tubular body, and primarily allow the device to uniformly expand out radially enabling the structure to orient itself into a helical structure upon deployment. In a more particular embodiment the S-curved bent is orientated substantially parallel to the longitudinal axis of the tubular body, which allows the member to uniformly expand perpendicular to said axis. This prevents the device from twisting and rotating on the balloon-catheter, or the like, as the device undergoes expansion.

The endoprosthesis may have a uniform structure throughout the device. An embodiment of the device is characterized in that the tubular body comprises a central portion, two outer portions at opposite ends of said tubular body and at least one intermediate portion in between the central portion and each of said end portions, the different portions being designed according to their specific function in the device. This embodiment is based on the recognition that different requirements may have to be imposed on different parts of the endoprosthesis to precisely meet the specific function or desired behaviour of the part concerned while the device is either unexpanded, expanded or in a transition between the unexpanded and expanded state. The present invention provides for a device in which this kind of tailoring may be implemented.

More particularly a further embodiment of the endoprosthesis is characterized in that at least in one of the two outer portions of the tubular body the undulations in said structure have a gradually decreasing amplitude whether or not in combination with a changing pitch or filament width in order to render a free end of said portion substantially transverse to the longitudinal axis of said body, at least in said first unexpanded state of said structure. Such a square-like tubular end of the endoprosthesis prevents an undesired cantilever protrusion of the last turn which otherwise could harm the wall of the lumen while the device is being navigated to its intended position. Moreover this structure improves the mechanical bond between the endoprosthesis and the balloon of the catheter used to manipulate the device within the body. The square end is created by gradually decreasing the amplitude and changing the pitch of the last few undulations until there is a final smooth transition forming the desired square end. Modifications of the filament width at this area may further improve this part's behaviour.

A still further embodiment of the endoprosthesis is characterized in that said central portion of the tubular body comprises a first number of connection elements per full helical turn of said at least one substantially helical pattern within said structure, in that at least one of said intermediate portions comprises a second number of connection elements of the structure per full helical turn of said at least one substantially helical pattern within said structure, and in that the first number of connection elements is smaller than said second number of connection elements imparting a difference in flexibility between both portions of the tubular body. More precisely, the central portion will exhibit more flexibility than the intermediate portions due to the lower number of interconnections between adjacent turns. To accommodate this difference within the structure, a specific embodiment of the endoprosthesis according to the invention is characterized in that the central portion and any one of said intermediate portions are separated from each other by a transitional portion in order to smoothly change the number of interconnections between adjacent turns from the first number to the second number of connection elements per full helical turn of said pattern.

In a more specific embodiment the endoprosthesis according to the invention is characterized in that adjacent turns in said central portion comprise a number of connection elements which are equally divided and in that connection elements in subsequent turns are helically shifted by approximately one undulation pitch distance. For example, there could be six adjoining helical segments with three equally spaced connection elements, situated approximately 120.degree. with respect to one another or six opposing helical segments with two equally spaced connection elements situated approximately 180.degree. with respect to one another. This specific design yields the most flexible structure in the central region, both crimped and deployed.

Once deployed, the structure will orient itself in line with the helical lattice structure which it forms, exhibiting three intertwining continuous lattice legs within the intermediate region and only two of those legs in the central region. The intermediate region will possess more stiffness in order to counteract the balloon expansion, known as the "dog bone effect", which causes the ends of the device to flare prematurely prior to the deployment of the central section and which results in an undue amount of foreshortening upon expansion. Moreover the intermediate regions serve as a relief between the end portions and the central region of the device.

The stents of the present invention may also comprise a generally cylindrically shaped main body having a plurality of expandable helical segments. The main body is comprised of a plurality of cylindrical main body elements that are joined together by the helical segments. The cylindrical elements have cylindrical axes that are collinear with the cylindrical axis of the main body. The cylindrical elements are formed from a plurality of circumferential elements that are joined together by the expandable helical segments. In some embodiments, the stent may comprise endzones that straddle the main body.

In one embodiment, the stent may comprise a first non-helical endzone and a second non-helical endzone that straddle the main body. The main body is generally cylindrically shaped and has a cylindrical axis. A plurality of adjacent main body cylindrical elements are connected together to form the main body of the stent. Each main body cylindrical element may be comprised of a plurality of expandable first and second circumferential elements. In some embodiments, the second circumferential elements have a circumferential dimension less than the circumferential dimension of the first circumferential elements. In yet other embodiments, the first and second circumferential elements have the same circumferential dimensions and are substantially identical except that, with respect to the cylindrical axis of the stent, they are oriented differently. Each second circumferential segment in each main body cylindrical element is connected to two first circumferential segments. In addition, each second circumferential segment in each main body cylindrical element is connected to a second circumferential segment in an adjoining main body cylindrical element thereby forming a plurality of helixes in the main body of the stent.

In one embodiment, the main body may be comprised of a plurality of first helical segments each having a substantially identical first pitch and a plurality of second helical segments, each having a substantially identical second pitch. The first and second pitches are generally different. In at least one embodiment, the second pitch is twice that of the first, and at least one first helical segment crosses one of the second helical segments.

The stents of the present invention may be manufactured from a tubular member by removing material from the tube to form a first endzone region, a second endzone region, and a middle region. By removing material from the middle region a plurality of parallel helical segments will remain and a plurality of circumferential segments will remain connecting the helical segments. Alternatively, the stent may be formed from a tube by removing material such that at least two sets of helical segments remain with each set having a different pitch.

BRIEF DESCRIPTION OF THE DRAWINGS

The present invention will now be further described in more detail with reference to the following figures in which like elements are provided with the same reference numerals.

DETAILED DESCRIPTION OF THE INVENTION

The present invention is directed to an expandable stent, as well as a method of manufacturing the stent.

Figure 1:
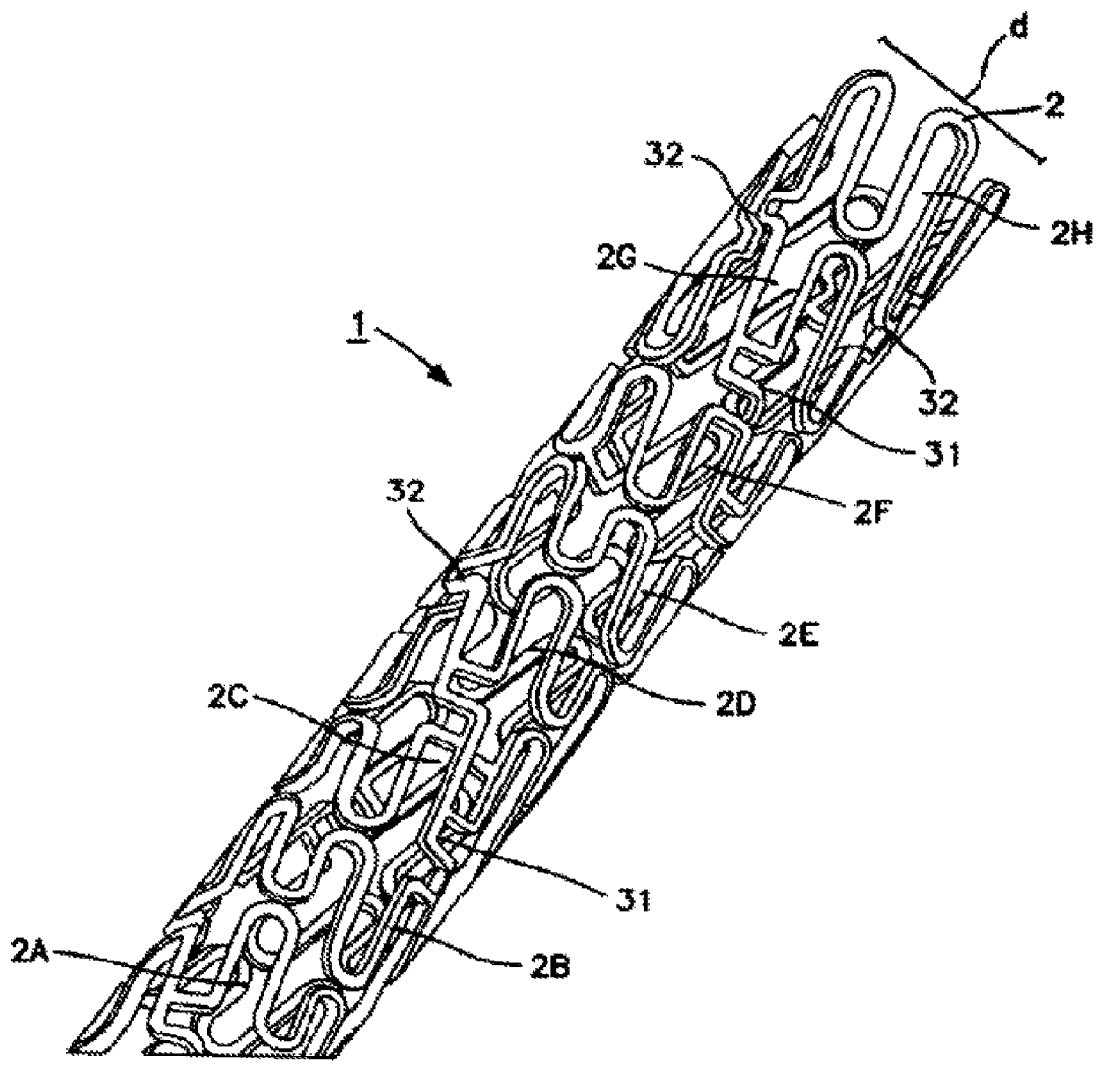
FIG. 1 shows an isometric view of an embodiment of an expandable intraluminal endoprosthesis in accordance with the present invention.

FIG. 1 gives an isometric view of an expandable intraluminal endoprosthesis according to a specific embodiment of the present invention. The endoprosthesis, hereinafter briefly referred to as stent, comprises a tubular member 1 which has been separated out of a tubular body of a suitable bio-compatible material. As such for instance high grade stainless steel (SST), a nickel-titanium based alloy referred to as Nitinol (NiTi), several cobalt based alloys and a Niobium-Titanium (NbTi) based alloy qualify. In this case the latter material may be chosen because of its excellent mechanical strength, corrosion resistance and radiopaque fluoroscopic signature. In the first, unexplained state shown, the tubular member 1 is drawn with a first diameter d which permits delivery of the member into a lumen of a body passageway, particularly a blood vessel. The member 1 is capable of acquiring a second, expanded and deformed diameter upon the application of a radially outwardly extending force from its interior, usually by means of a balloon-catheter. This second diameter is variable and dependent on the amount of force applied. Inevitably the member will show a certain amount of recoil which means that the device will retract more or less after the balloon has been evacuated. Accordingly the second diameter will be slightly smaller than the diameter to which the stent has been expanded. Nevertheless the tubular member may be expanded and deformed to expand the lumen of the body passageway to again assure an undisturbed flow through the lumen, like a blood vessel.

The wall of the stent comprises a substantially continuous structure which in this example consists of a continuous filament which has been cut out from the tube wall in a substantially helical fashion with a width between about 0.10 and 0.17 mm. This may be done by means of laser cutting, electrochemical etching, electromechanical discharge or any other suitable technique preferably followed by a suitable surface treatment, like etching to deburr and or round off possible sharp edges. In this example a tubular body with an internal diameter of about 3.0 mm, a wall thickness of about 1.0 mm and a length of about 30 mm has been chosen as a starting material. However, other dimensions are likewise feasible within the scope of the present invention. Particularly the length may be adapted to the diseased part of the lumen to be stented in order to avoid the necessity of separate stents to cover the total area. The filament-structure comprises a number of undulations 2 which are mutually staggered in helical pattern advancing around a central longitudinal axis of the device. In order to retain a coherent body subsequent turns 2A 2H of the filament are interconnected by means of one or more connection elements 31,32 which are entirely integral with the undulations thereby connected, as they are cut altogether from one and the same tubular body. To retain flexibility, both unexpanded as well as deployed, the number of connection elements per helical turn is less than the number of undulations in said turn. This is further elucidated in FIG. 2 which gives plan view of the device as if it were cut open. As emerges quite clearly from this figure, the connection elements 31 to subsequent turns are radially shifted by about half undulation pitch distance ½L to form a helical pattern X-X, Y-Y. Once deployed, these patterns will expand to a helically turning spines which form a primary framework or scaffolding lattice of the deployed stent. This framework supports the vessel wall highly uniformly throughout the device and moreover is capable of withstanding substantial inwardly directed radial forces. This capability of the framework is referred to as its hoop strength.

Figure 2:
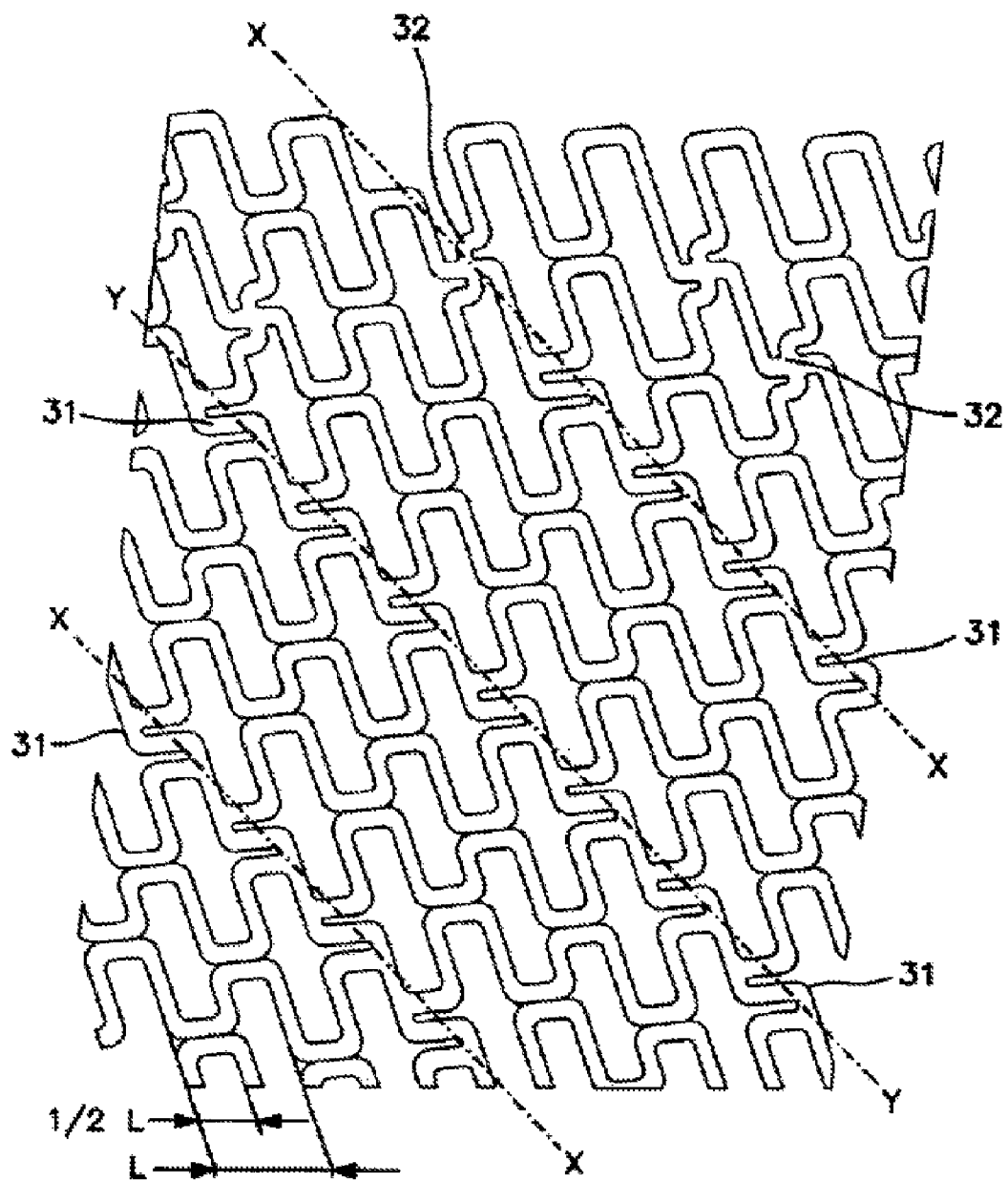
FIG. 2 is a plan view of the endoprosthesis of FIG. 1.

The lower drawing part of FIG. 2 shows a part of a central modular portion of the device in which successive turns of the filament are interconnected by means of only two connection elements 31, which are shifted about 180° with respect to one another, while the upper part shows an end portion of the device together with an intermediate portion in which three equally spaced connection elements 31, 32 interconnect adjacent undulations from successive turns of the filament with each other. As a result the parent scaffolding lattice of the deployed device will be composed of only one helically advancing spine within the central region and will comprise two helically revolving spines within the other regions. Although the latter provides less flexibility, it leads to an improved adhesion to the balloon-catheter by which the device is guided through the lumen and moreover counteracts a so-called dog bone effect, which is a premature expansion at the tail ends of the device. The central portion of the device, i.e. the lower drawing part, one the other hand retains maximum flexibility and conformability due to the smaller number of interconnections between adjacent undulations within this segment.

In this example two kinds of connection element are used, denoted 31 and 32 respectively. Both types of connection elements feature a strut 3 which is S-shaped and diagonally interconnects opposite sides of adjacent undulations from successive turns of the filament in a helical direction different to that of the staggered undulations themselves, see also FIG. 3E. These struts will be referred to as major struts as they are part of the lattice spines described hereinbefore. The struts will be referred to as major struts as they are part of the lattice spines described hereinbefore. The second type of interconnection element 32 moreover features a second, S-shaped diagonal 4 strut intersecting the first one, see also FIG. 3D. Due to this shape an interconnection element of the second kind 32 will first start to rotate around its central axis once the stent is being deployed with only a limited force being exerted axially in the diagonal 3 of the connection element. Only after the first diagonal 3 has become fully in line with the sides of the undulations it interconnects, does it have to withstand the entire force axially. This incorporated slack and stress relief allows thinner strut width and filament width over the lattice legs which can be useful for decreasing the radio-opacity at this area as well as improves its unexpanded, crimped as well as deployed, expanded flexibility. Moreover the support area covered by connection elements of this second kind will not decrease much upon deployment of the device. As a result a larger "scaffolding footprint" will remain after deployment compared to any of the other types of connection elements shown which all will stretch substantially upon deployment leaving only the thin major strut 3 as "scaffolding footprint".

Besides the types of connection elements depicted in the drawing, other shapes are also feasible, as the invention imposes hardly any limitation of the design of any part of the device including the shape of the interconnections used. Examples of other shapes which could advantageously be used in a device according to the invention are shown in FIGS. 3A 3G. The connection elements of FIGS. 3A 3C merely comprise a straight strut 3 connection adjacent undulations, whereas the main strut 3 of the connection elements shown in FIGS. 3D 3F have a clearly S-curved shape. This shape introduces more slack and expandability in the structure. The longer this segment, the more slack and expandability there is in the structure and especially in the spinal ladder created by these connection elements in the eventual deployed device. A simple formula can be derived from the expanded state, defining the relative increase of the strut length and the effect it has on the expansion range of the device.

Figure 3:
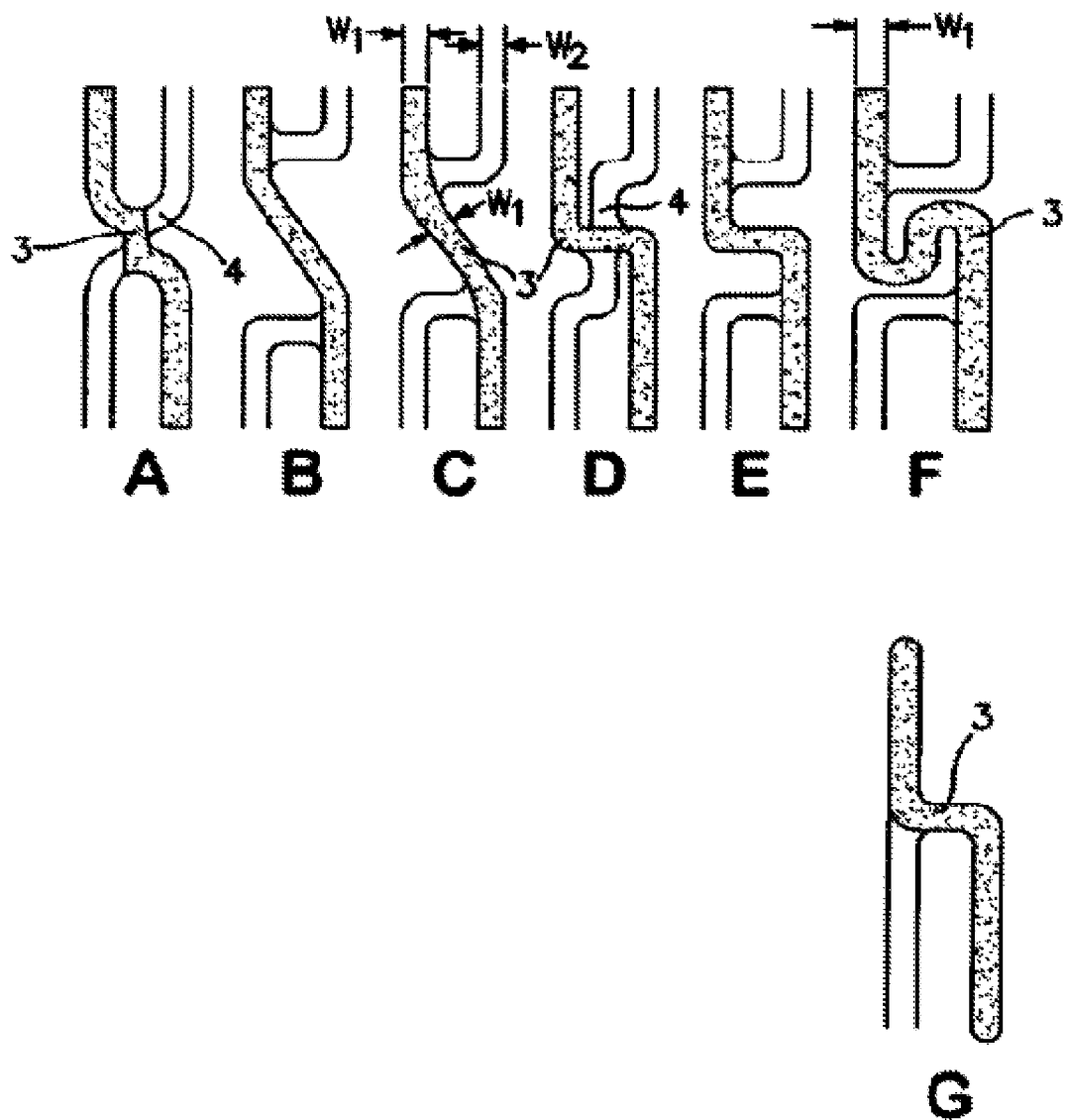
FIG. 3 shows alternative embodiments of interconnection elements to be in a device according to the invention.

The major strut 3, i.e. the strut eventually forming part of the parent scaffold or framework of the device once it is deployed, is indicated in FIG. 3 by a dotted hatch. In a special embodiment this strut as well as the undulation sides which it interconnects are given a first filament width $w_1$ sufficiently large to withstand the axial forces imposed thereon during expansion of the device, whilst the other undulation sides and if applicable the other strut of the connection element are given a second filament width $w_2$, at least locally, to gain flexibility and decrease radio-opacity. Specifically the filament width is modified in the central portion of the device to improve its overall flexibility such that a first filament width $w_1$ of approximately 0.14 mm is taken whereas the second filament width $w_1$ is reduced to about 0.11 mm.

In order to avoid a substantial disruption of the stent to vessel support by pairs of undulations from successive turns of the filament which are not mutually interconnected by a connection element, the amplitudes of the undulations within such pair may be adapted to fill the gap which would otherwise remain due to the inevitable length of a connection element elsewhere in the structure. This is for instance apparent from FIG. 2 where all adjacent peaks and valleys of pairs of undulations out of successive turns which are not interconnected nevertheless adjoin one another. This is a result of the adapting the amplitude of at least one of the undulations within such pair of undulations. This can imply that both, the peak and the valley have an increased amplitude, that only one of those parts is enlarged, the other part remaining unchanged, or even that either the peak or the valley has a increased amplitude while the other part has a decreased amplitude. Also in this respect, the designer has full freedom to tailor the stent design to allow optimal behaviour of the stent in its unexpanded state, expanded and/or transitional state.

Figure 4:
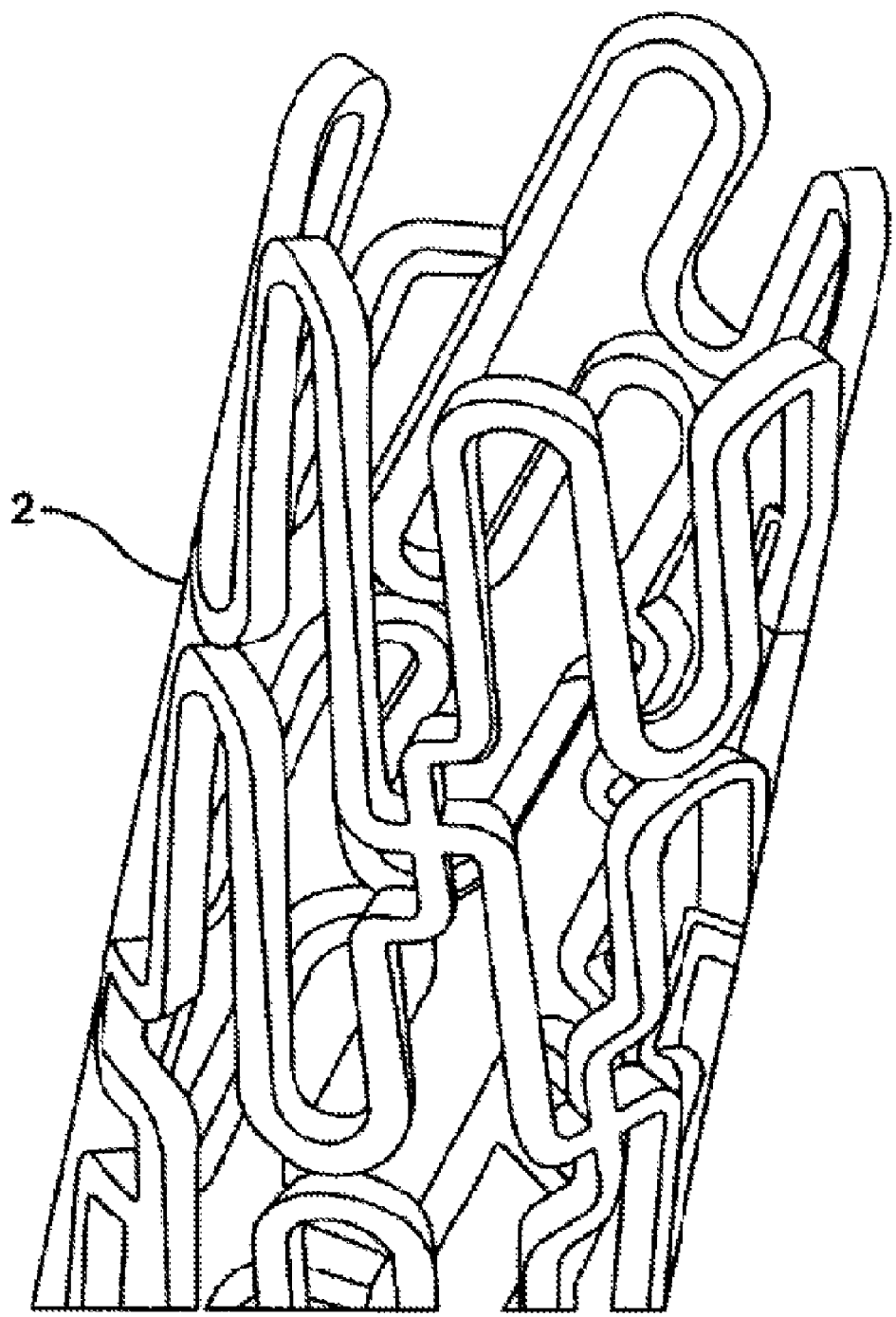
FIG. 4 is an enlarged view of an end portion of the endoprosthesis of FIG. 1.

The end portion of the device ends substantially transverse to the central axis of the device in order to avoid a cantilever usually associated with a helix shape which could otherwise harm the wall of the lumen through which the stent is navigated. This end portion is shown in more detail in FIG. 4. Its particular shape is obtained by gradually decreasing the amplitude in the last few undulations and adapting their mutual pitch. Due to the invention this may be done without introducing any stress in the device as the filament is simply cut in the desired pattern. The deviating amplitudes and mutual pitch are best recognized from the plan view of FIG. 2. The end modules exhibit a greater stent-to-vessel ratio than the central and intermediate portions due to the increased metal-to-surface-area in the expanded configuration. The more complex structure of the end portions moreover give rise to a greater amount of foreshortening upon expansion, thus producing a more dense pattern yielding additional stent-to-vessel ratio.

Figure 5:
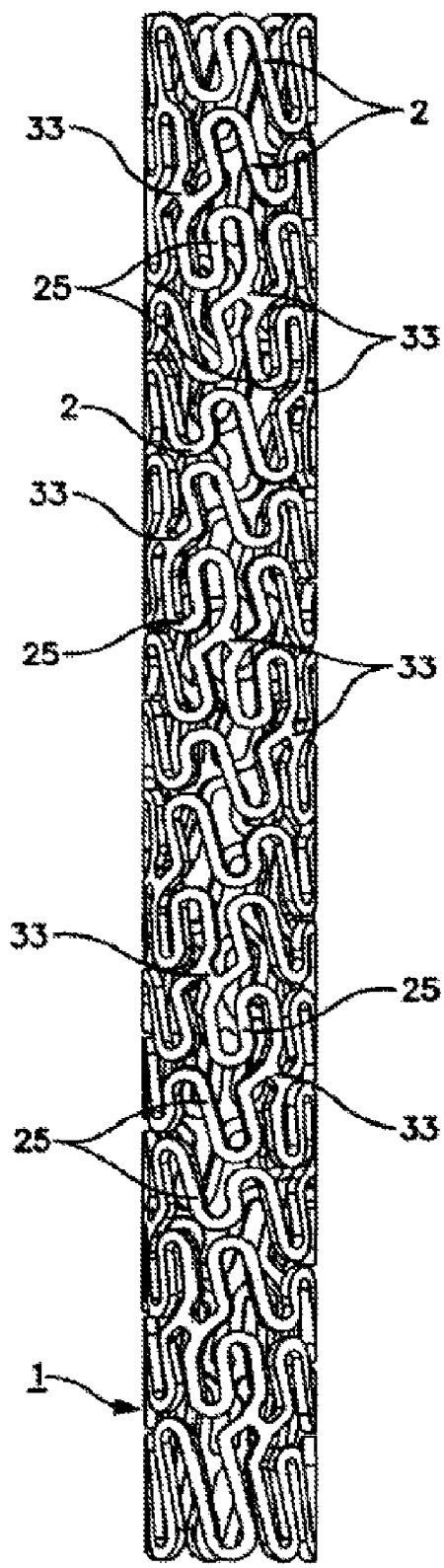
FIG. 5 shows an isometric view of a second embodiment of an expandable intraluminal endoprosthesis in accordance with the present invention.
Figure 7:
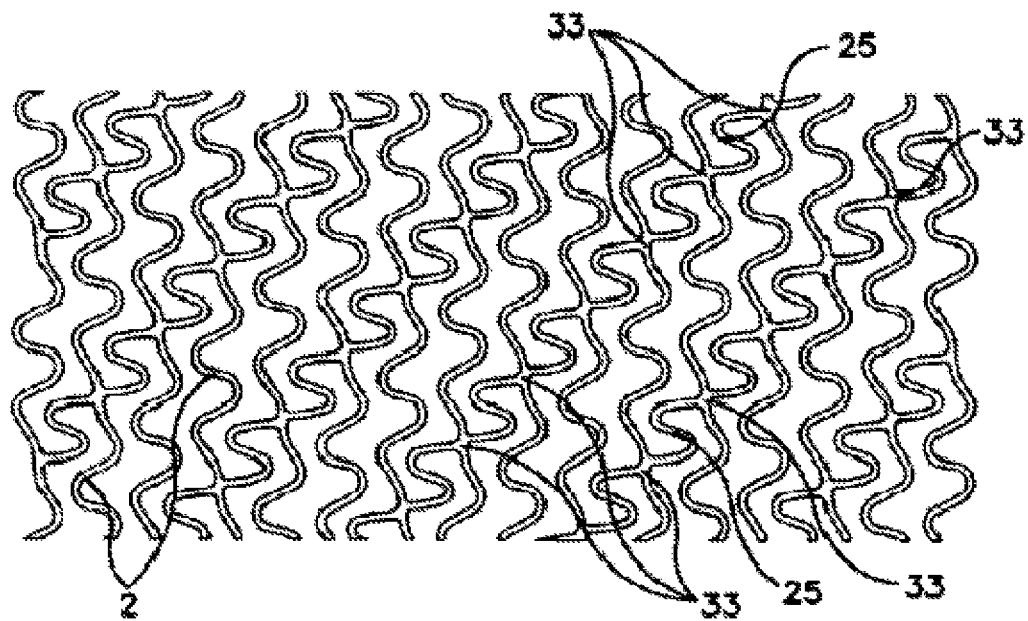
FIG. 7 is a plan view of the device of FIG. 5 in a expanded, deployed state.

A second embodiment of the device according to the invention is depicted in FIGS. 5 7. This device comprises a tubular body 1 and has been manufactured using similar techniques as in the first embodiment, although in this case a more complicated structure has been created consisting of more than just a single, wrapped filament. However, like in the first embodiment, the structure of the device is composed of a substantially helical pattern of mutually staggered undulations 2, with connection elements 33 interconnecting some undulations from successive turns of said pattern. The connection elements within this structure primarily comprise two intersecting struts like the type reflected in FIG. 3D.

Figure 6:
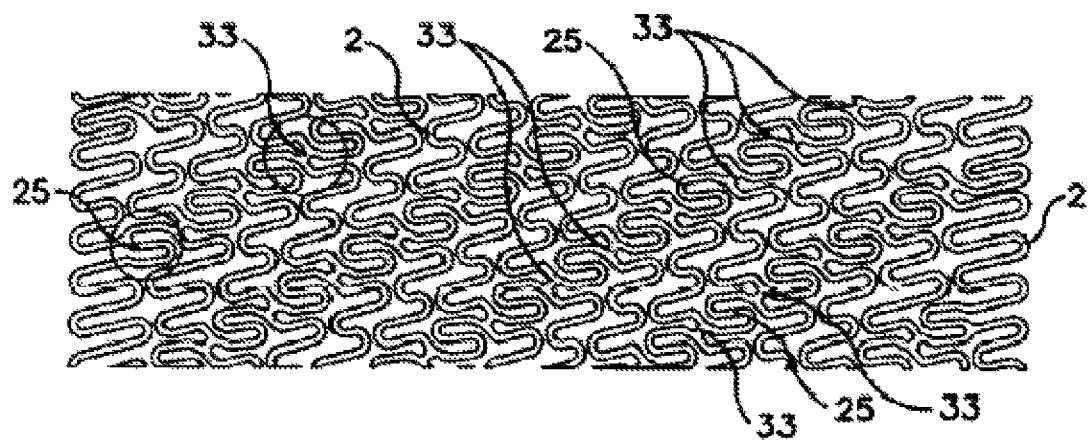
FIG. 6 shows a plan view of the device of FIG. 5 in a unexpanded state.

Different to the structure of the first embodiment, connection elements 33 to subsequent turns of said pattern are shifted by about a full pitch distance. As a result a full undulation 25 will link said connection elements 33 to one another and as such creates an elongated member 25 in between the connection elements 33. Said elongated member formed by an intermediate undulation comprises a S-curved bent and is longer than the linear distance between the interconnection elements thereby linked to each other, at least in the crimped state shown in FIGS. 5 and 6. This imparts additional slack and considerable expandability to the spinal ladders which are formed by such a series of linked connection elements in the deployed state shown in FIG. 7. Moreover the orientation of the S-curved bents in said elongated members 25, which is substantially parallel to the longitudinal axis of the body at least in the crimped state shown in FIGS. 5 and 6, allows the member 25 to uniformly expand in a direction which is substantially perpendicular to said axis. This prevents the device from twisting and turning on the balloon-catheter once it is being expanded.

Like in the first embodiment, also in this case said series of interlinked connection elements mutually shifted by a pitch distance, form further substantially helically advancing patterns within the structure. Like the staggered undulations themselves, these further helically revolving patterns will mature to helical spines running through the structure once it is being expanded, see FIG. 7. These additional spines however run in a different direction than the spines created by the undulations, indicated by the straight lines in FIG. 7, which results in an eventual structure with a considerable hoop strength in combination with an excellent unexpanded and deployed flexibility. As the device of the invention allows for a very large design freedom, these aspects may be once more tailored throughout the device to fit the best overall characteristics in each portion of the device.

Although the invention has been described hereinbefore with reference to merely a few embodiments, it will be appreciated that the invention is far more wide spread applicable. Within the scope of the invention many other embodiments and variations are feasible for a skilled practitioner. As such he may vary for instance the mutual pitch of a few or more subsequent undulation with or without a variation of the amplitude in order to tailor the stent-to-vessel ratio and flexibility at the area concerned. Also, additional modular portions individually recognizable in the stent could be implemented in the stent in order to add specific functionality. As such, a transitional portion might be interposed between the relatively flexible central portion and the more stiff intermediate and end portion in order to alleviate the structural transition between those parts of the stent. Also the number of connection elements within a full turn of the helical pattern may be raised to introduce additional lattice spines to the deployed device, resulting in even a larger hoop strength and supporting capability of the device.

Likewise, the filament width as well undulation shapes may be varied and adapted to suit specific required characteristics besides the flexibility and stent-to-vessel ratio. For instance, the foreshortening of the device, i.e. the amount of length reduction upon expansion from the crimped to the deployed state of the device, its degree of recoil, its hoop strength as well as it radio-opacity may be so varied and adapted. In any event the present invention provides the designer with the greatest amount of freedom conceivable.

Also the elongated members interlinking a series of connections elements like in the second embodiment need not coincide with undulations of the pattern and can be introduced in the structure as separate elements. These members moreover need not necessarily comprise a full S-curved bent or even any S-curved bent at all and may on the other hand consist of more than just one such bent. Also in this respect the designer has total freedom to tailor the device to his demands.

Figure 8:
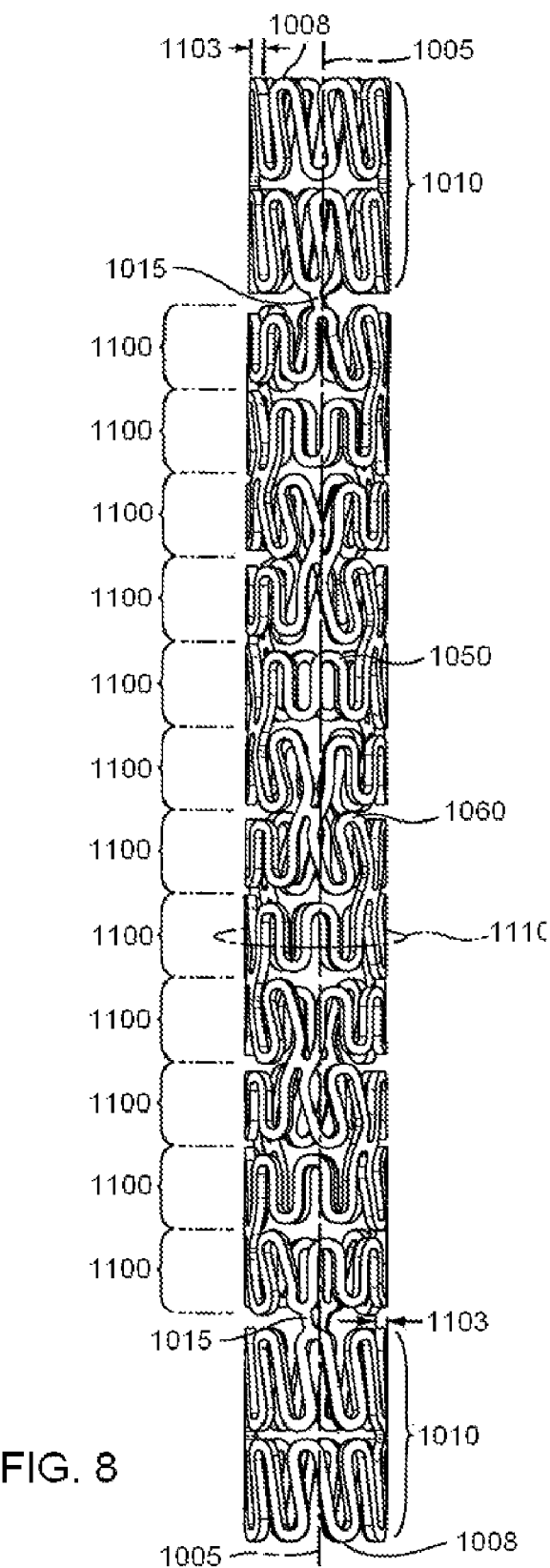
FIG. 8 is a three dimensional view of one embodiment of a stent according to the present invention in its unexpanded state.
Figure 9:
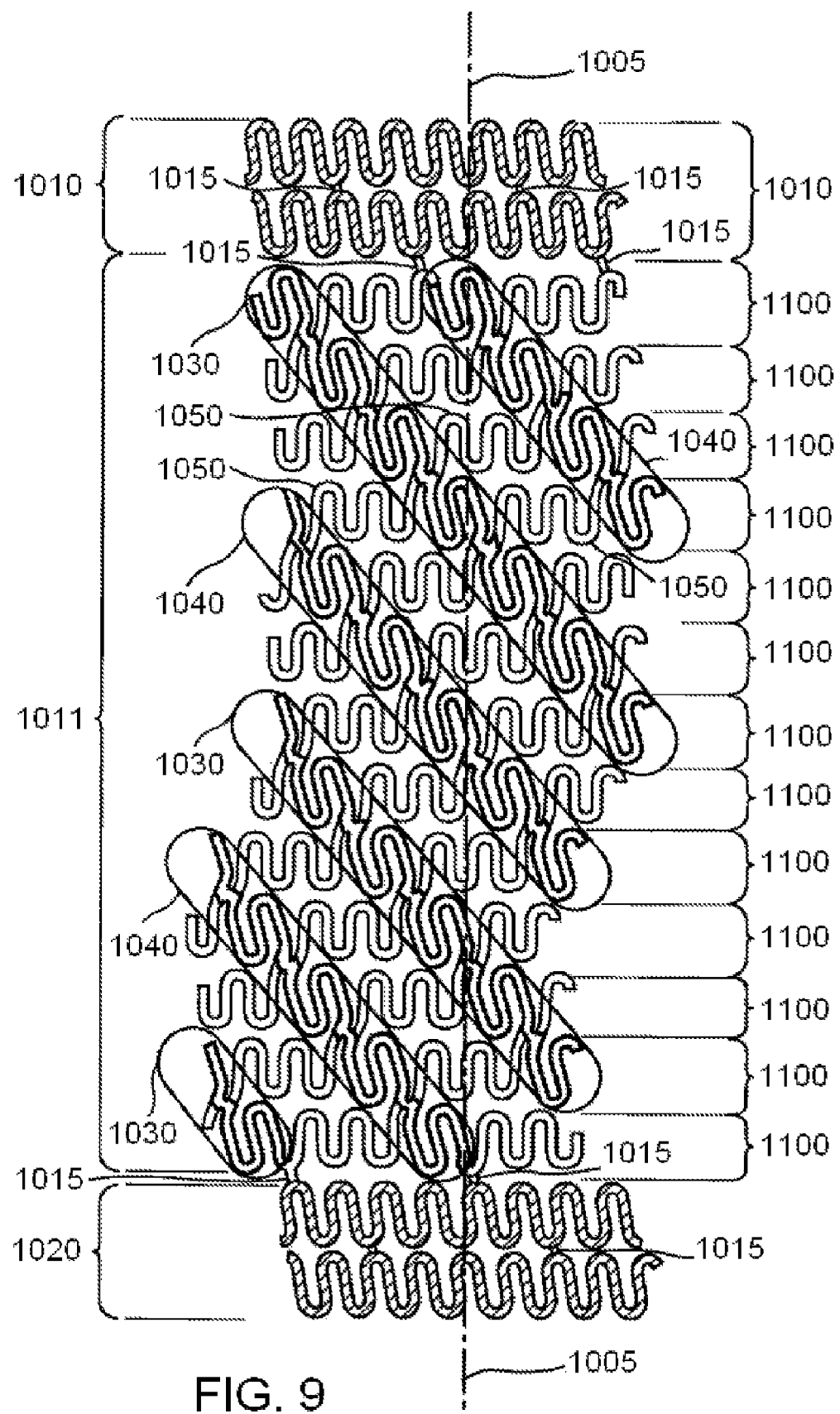
FIG. 9 is planar view of a flattened portion of the circumference of the stent in FIG. 8.

In one embodiment, as is shown in FIGS. 8 and 9, the stent comprises a generally cylindrical shaped main body section 1011 having a cylindrical axis 1005 and a wall thickness 1103. The wall thickness 1103 may optionally be uniform throughout the stent. The main body section 1011 is comprised of a plurality of helical segments 1030 and 1040 and a plurality of main body cylindrical elements 1100, each having cylindrical axes (not shown) that are collinear with the main body cylindrical axis 1005. The main body cylindrical elements 1100 are each comprised of circumferential elements 1050 that are joined together by the helical segments 1030 and 1040 to form individual cylinders 1100.

The stent may also have a first endzone 1010 and a second endzone 1020 that straddle the body section 1011. In some embodiments, such as the one shown in FIG. 8, the endzones 1010 and 1020 may advantageously provide the stent with square outer edges 1008. The stent may be manufactured from stainless steel, or other suitable materials. In most embodiments, it is desirable that the material, or a portion of the material, be radiopaque and that the various segments that form the stent be contiguous. Although, in some embodiments, the various segments that make up the stent can be distinct elements that are joined together.

The main body 1011, shown in FIGS. 8 and 9, may be formed in numerous ways. For example, the body 1011 may contain two or more first helical segment 1030 and 1040 that are generally parallel to each other. In some embodiments they may be opposite each other by 180 degrees. In general, the first helical segments 1030 and 1040 will be spaced equidistant along the circumference 1110 of the main body 1011. The first helical segments 1030 and 1040 are joined by a plurality of circumferential segments 1050 to form a plurality of main body cylindrical elements 1100, which may be only generally cylindrically shaped. In one embodiment, the circumferential segments 1050 make up a majority of the circumference 1110 of each cylindrical element 1100. In addition to joining the circumferential elements 1050 to form cylindrical elements 1100, the helical segments 1030 and 1040 connect each cylindrical element 1100 to an adjacent cylindrical element 1100 to form the main body 1011.

Figure 10:
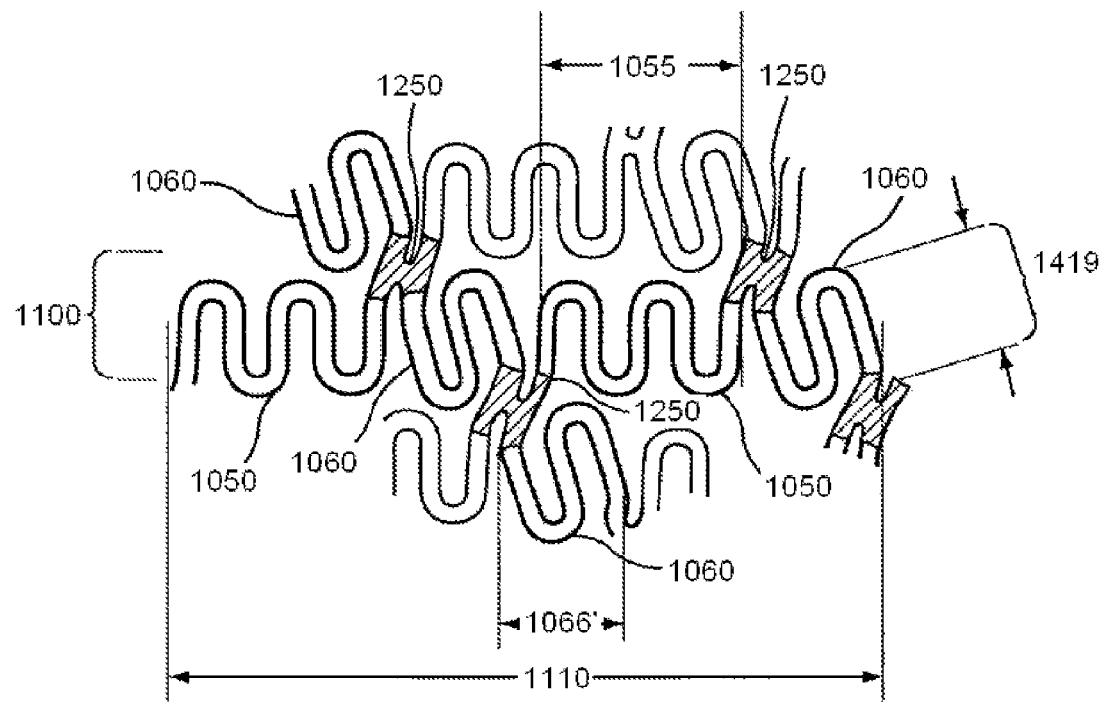
FIG. 10 is an enlarged portion of FIG. 9.
Figure 12:
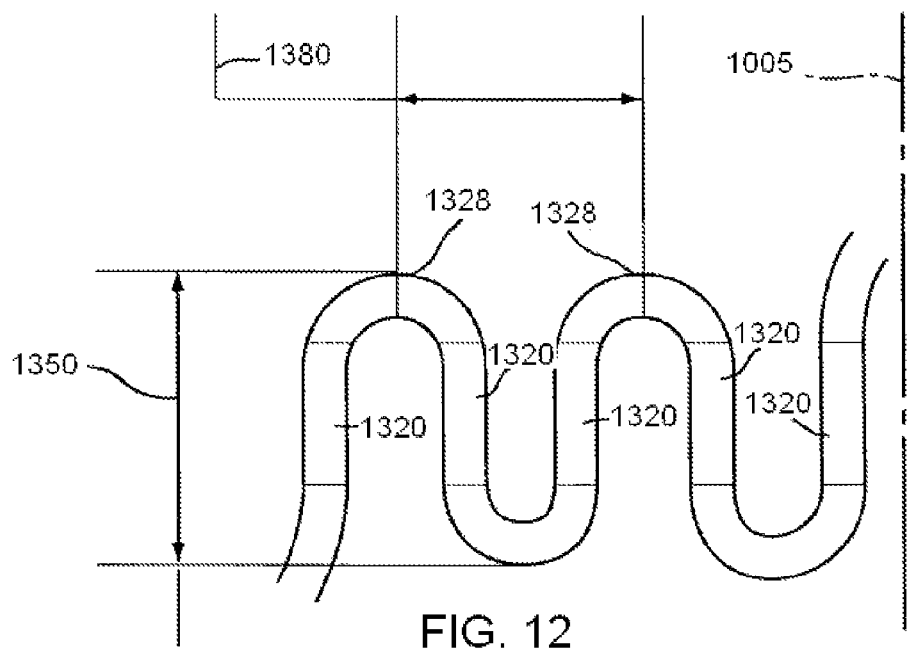
FIG. 12 is an enlarged view of a portion of FIG. 11 showing a first circumferential element of the stent.

As is shown in FIGS. 9 and 10, the body of the stent 1011 may comprise a plurality of main body cylindrical elements 1100 formed from first circumferential segments 1050 that are joined with second circumferential segments 1060. The second circumferential segments 1060 of each cylindrical element 1100 may be joined with second circumferential segments 1060 of adjacent cylindrical elements 1100 to form a plurality of first helical segments 1030 and 1040 in the main body 1011. (See FIG. 9). Each first circumferential segment 1050 may have a circumferential dimension 1055 and each second circumferential segments 1060 may have a circumferential dimension 1066' (See FIG. 10). In some embodiments, it may be desirable for the circumferential dimension 1055 of the first expandable element 1050 to be larger than the circumferential dimension 1066' of the second expandable element 1060.

The first circumferential segment 1050 may be an expandable segment formed from plurality of segments joined together to form a pattern. The pattern, such as the one shown in the FIGS. 8-10, may be a repeating pattern that resembles a square wave form having curved peaks and valleys. Other patterns, both repeating and non-repeating, may be used. For example, and without limitation, the first circumferential segments 1050 may resemble a triangle wave form, a sinusoidal wave form, other repetitious patterns, or any pattern that enables the segment to expand when a radial force is exerted on the stent from the inside or collapse radially when an external crimping force is applied.

Figure 11:
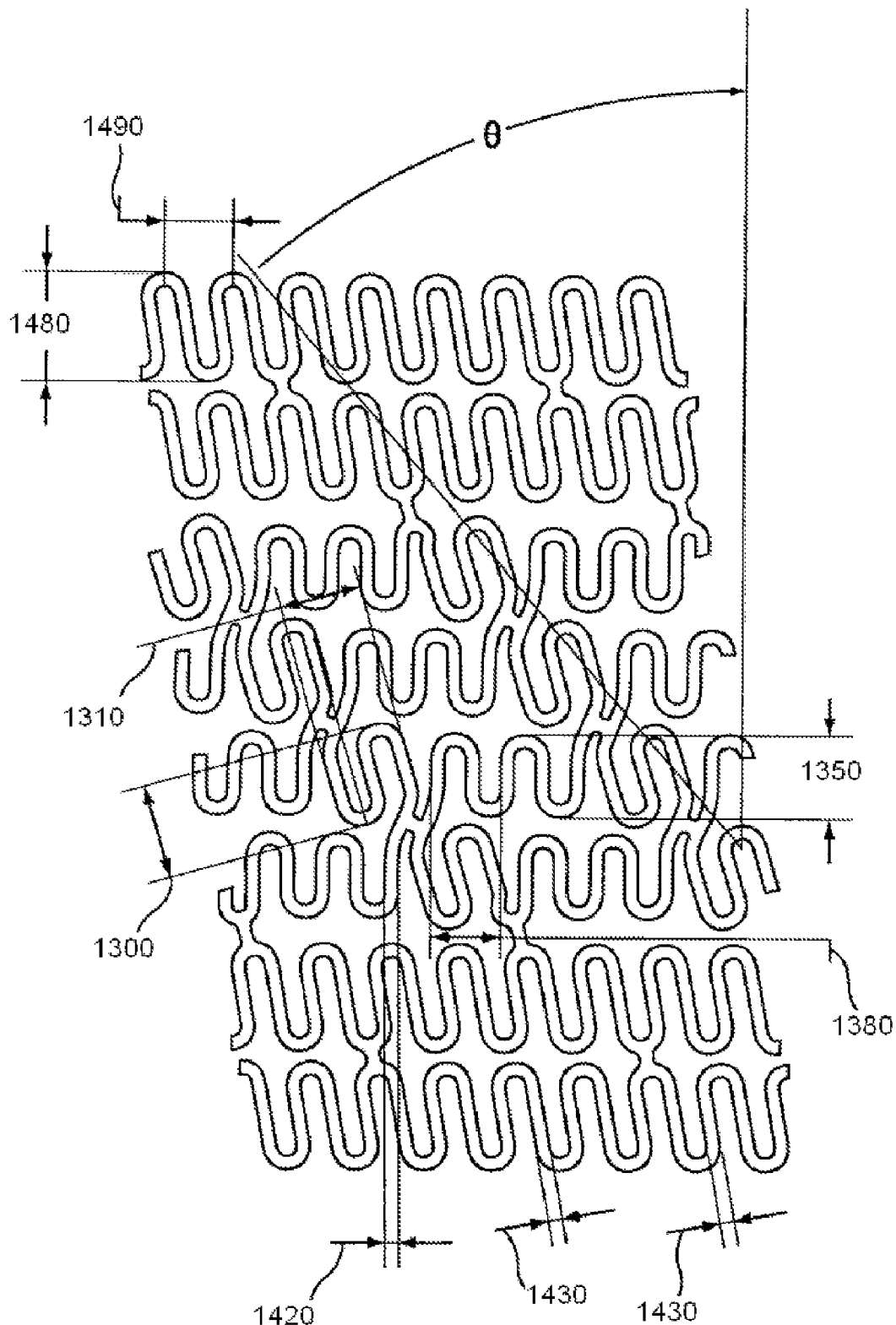
FIG. 11 is another planar view of a flattened portion of the circumference of a stent according to the present invention in its unexpanded state.

The first circumferential elements 1050 may have a filament width 1420 (see FIG. 11). In one embodiment, the filament width may vary between 0.002 inches and 0.007 inches, but is preferably about 0.0050 inches. Other filament widths may be used depending on the parameters of the stent.

In the embodiment shown in FIGS. 8-12, the first circumferential elements 1050 comprise linear portions 1320 and curved portions 1328 that join the linear portions 1320 together to form a repeating pattern. In some, but not all, embodiments, the linear portion 1320 may be parallel to the cylindrical axis of the stent. In other embodiments, the linear portion 1320 lies at an angle of between 0-45 degrees with respect to the cylindrical axis. The first circumferential segment 1050 has an amplitude 1350 and a period 1380. In one embodiment the amplitude may range from 0.5 mm to 2.0 mm and the period may range from 0.5 mm to 2.0 mm. In some embodiments, the amplitude is less than the period. Other amplitudes and periods may be used depending on the overall stent design and performance constraints.

Figure 13:
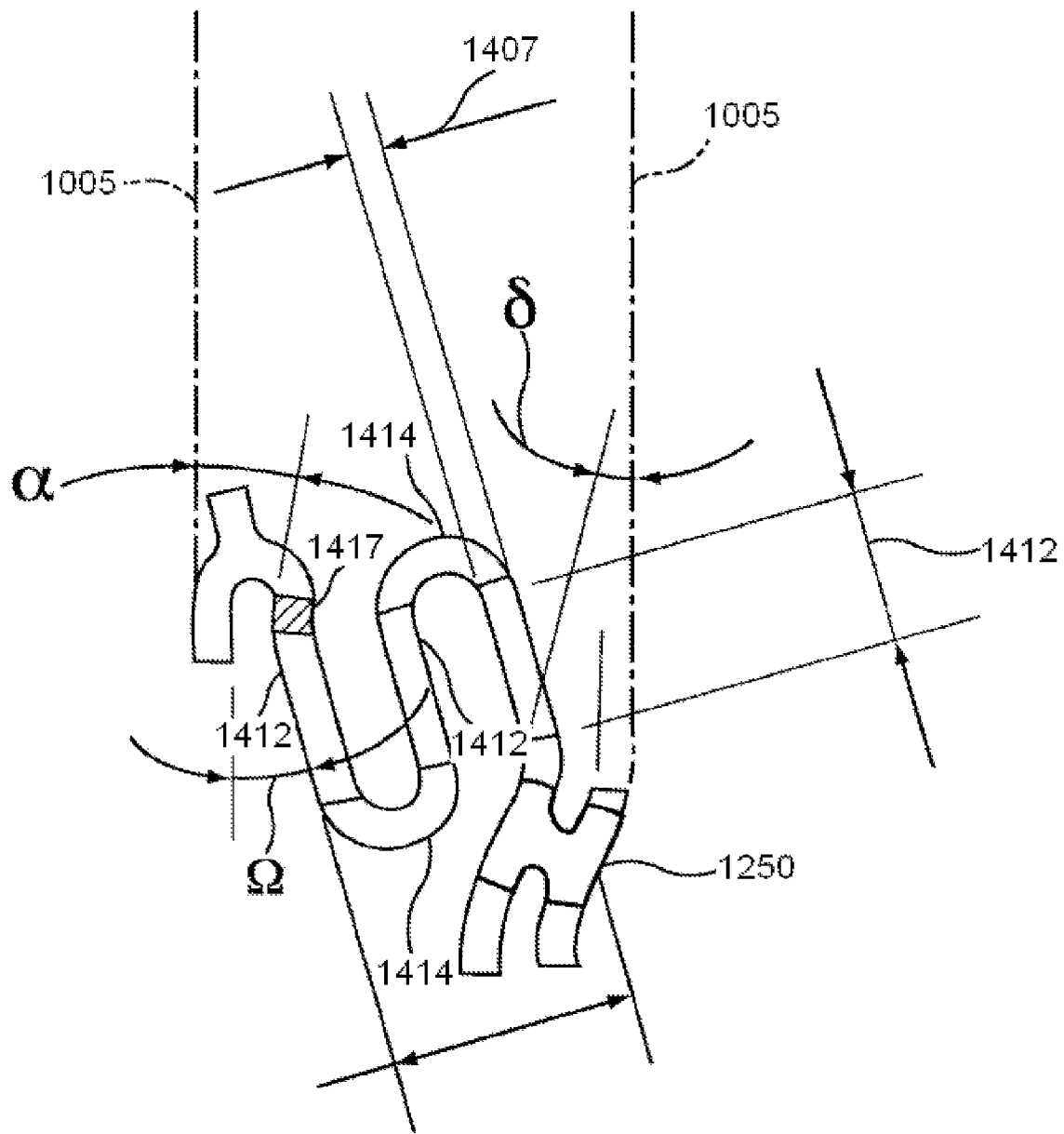
FIG. 13 is an enlarged view of a portion of FIG. 11 showing a second circumferential element of the stent.

The second circumferential element 1060, which may be joined together in a helical pattern to form one or more helical segments 1030 or 1040, may also take numerous forms, in addition to the form shown in FIG. 13. In the embodiment shown in FIG. 13, the second circumferential element 1060 comprises linear portions 1412 and curved portions 1414 having a filament width 1407, and resembles generally an S-shaped structure. In addition, the second element circumferential segment 1060 may have an angled portion 1417 attached to the linear portion 1412 at an end opposite that of the curved portion 1414. The angled portion may be oriented to form an angle $\alpha$ relative to the cylindrical axis of the stent 1005 in the range of 0-45 degrees. In at least one embodiment, the preferable angle $\alpha$ is about 10 degrees. In some embodiments, the linear portions 1412 of the second circumferential element 1060 lies at an angle $\Omega$ relative to the cylindrical axis of the stent, wherein $\Omega$ preferably ranges from 0 to 45 degrees. When viewed in a planar fashion as in FIG. 9, the linear portions 1412 may, in some embodiments, form an angle $\Omega$, relative to the cylindrical axis of the stent. In some embodiments, $\Omega$ may be approximately equal to the helical angle of the first helical segments 1030 and 1040. In one embodiment, the second circumferential elements 1060 may have an amplitude 1300 (see FIGS. 10, 11, and 13) ranging from 0.5 mm to 2.0 mm and a period 1310 ranging from 0.5 mm to 2.0 mm. Other ranges may be used depending on the particular stent size and design being employed. In one embodiment, the preferred period is about 0.82 mm and the preferred length of the linear portion 1412 is about 0.5 mm and the amplitude 1300 is about 0.38 mm. The amplitude of the second circumferential element 1060 may be greater than, equal to, or less than the amplitude of the first circumferential element 1050. In one embodiment, the circumferential contributions of the first circumferential elements 1050 to the overall circumference of the main body 1011 is greater than the circumferential contribution of the second circumferential element 1060, in terms of either circumferential length or circumferential cylindrical surface area. In one embodiment, the stent may have an overall outer surface area of about 0.029 square inches.

Figure 14:
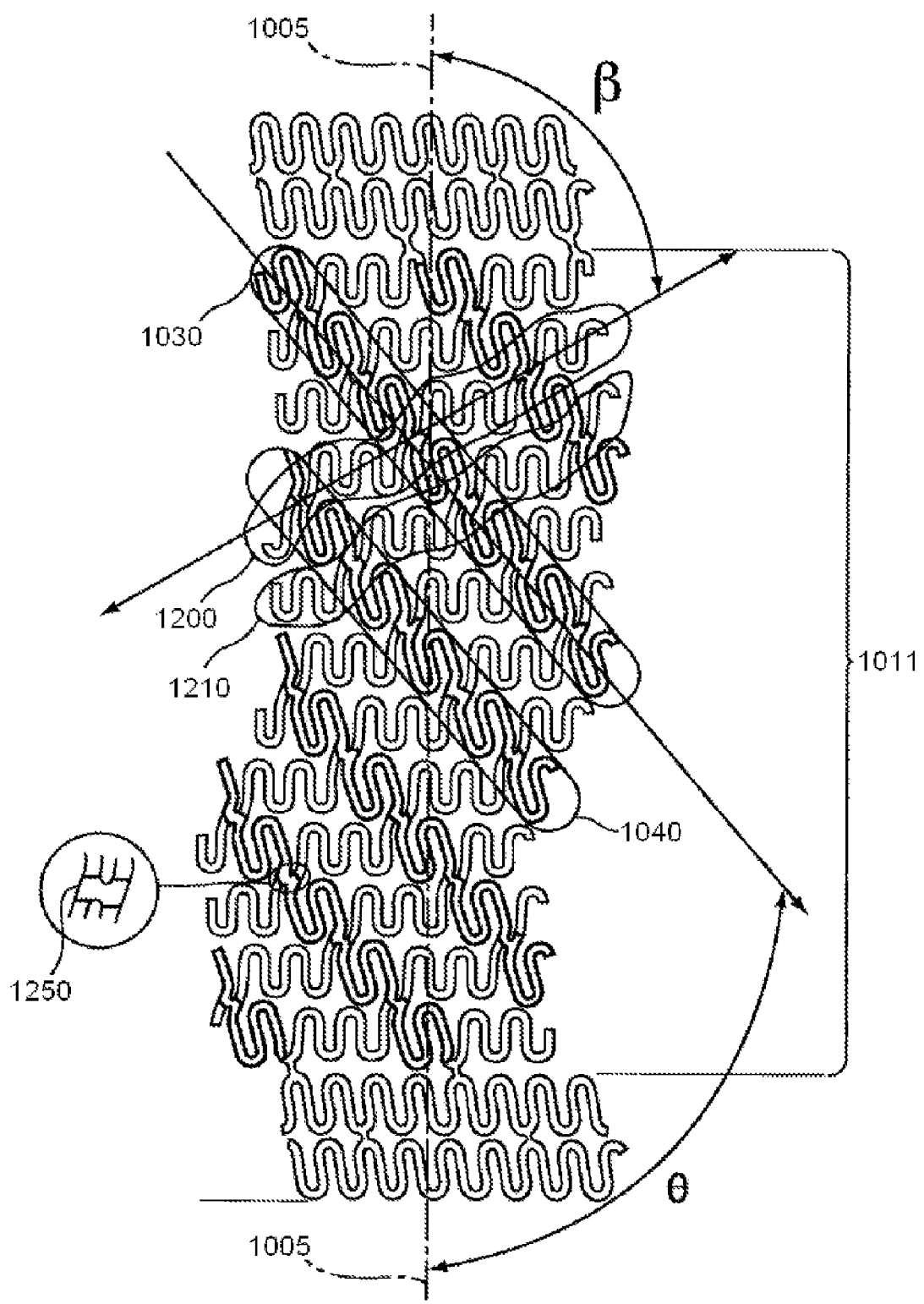
FIG. 14 is a planar view of a flattened portion of the stent in FIG. 8 showing a plurality of sets of helical segments propagating through the stent's body.

As is shown in FIG. 14, the stent may have a main body 1011 comprised of two or more first helical segments 1030 and 1040, as well as two or more second helical segments 1200 and 1210. The first and second helical segments 1030, 1040 and 1200, 1210, respectively, are joined together to form a generally cylindrically shaped body 1011. In some, but not all embodiments, the first and second helical segments may share a common connecting element 1250. In some embodiments, the common connecting element 1250 may be H-shaped and the two generally parallel linear portions of the H-shaped connecting segment 1250 may form an angle $\delta$ relative to the axis 1005. (See FIG. 13). $\delta$ may, in one embodiment, be about 14 degrees. As is shown in FIG. 14, the first helical segments 1030 and 1040 and second helical segments 1200 and 1210 may have different pitches, i.e. number of spirals per unit length, which results in the first and second helical segments as having different helical angles ($\theta$ and $\beta$, respectively) i.e. the angle of the helical segment relative to the cylindrical axis 105 of the stent. In one embodiment, the second helical segments 1200 and 1210 have a pitch approximately twice that of the first helical segments. In one embodiment $\theta$ may vary from 0 to 45 degrees and is preferably about 40 degrees and $\beta$ is preferably about twice $\theta$. In other embodiments the angle $\theta$ may range from 0 to 90 degrees to the circumference 1110 of each cylindrical element 1100.

As is shown in FIGS. 9, 10, 11, and 13, the helical segments 1030, 1040 are circumferentially expandable (i.e. they expand along the circumference of the stent) and may be formed from a plurality of circumferential elements 1060 that in turn are made up of linear 1412 and/or curved 1414 segments (see FIG. 13) that each have a filament width 1407 (see FIG. 13) that is less than the circumferential dimension 1066 of the circumferential element 1060 (see FIG. 10). In some embodiments, each helical segment 1030 or 1040 will make a total contribution to the circumference of each cylindrical element 1100 that is greater than the filament width 1407. The circumferential contribution of each helical segment 1030 or 1040 to the overall circumference of the stent (1110 in FIG. 8 or 1105 in FIG. 18) may be greater than the circumferential contribution of the filament widths 1407 of the segments (e.g. 1412 and 1414) making up the circumferential elements 1060 that in turn make up the helical segments. (I.e., In some embodiments the circumferential contribution of the helical segments 1030 and 1040 to the circumference 1110 of each cylindrical element 1100 is more than just a function of the filament width 1407, e.g., it may be a function of the geometry of the element 1060.) For the embodiment shown in FIGS. 8 and 18, this is the case when the stent is in both the unexpanded and expanded state. The geometry of the helical segments 1030 and 1040 are a factor in determining their expandability.

Likewise, the helical segments 1200, 1210 are circumferentially expandable and may be comprised of other circumferential elements 1050 that are in turn comprised of linear 1320 and/or curved segments 1328 (see FIGS. 10 and 12) that have a filament width 1420 (see FIG. 11). The contribution of the helical segments 1200, 1210 to the overall circumferential dimension 1110 of each cylindrical element 1100 is greater than just the contribution of the filament widths 1420 of the individual segments 1320 and 1328 that make up the elements 1050 that in turn make up the helical segments 1200, 1210. The geometry of the elements 1050 making up the helical segments 1200, 1210 may be a more important factor in determining the circumferential contribution of the helical segments 1200 and 1210 to the overall stent circumference than the filament width 1420. Thus, in one embodiment of the present invention, the circumference of the stent 1110 in its unexpanded state and the circumference 1105 when the stent is expanded are primarily functions of the geometry of the elements 1050 and 1060 that make up the helical segments 1030, 1040 and 1200, 1210, respectively.

Figure 15:
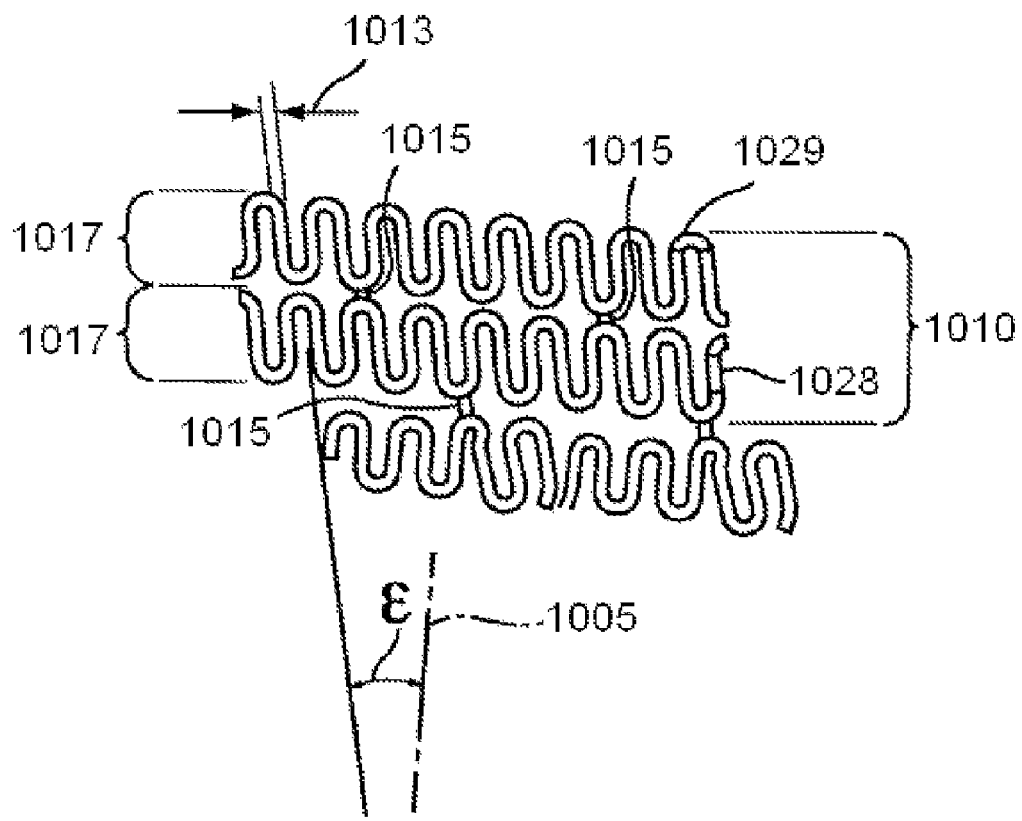
FIG. 15 is a planar view of a flattened endzone that may be employed in a stent of the present invention.
Figure 16:
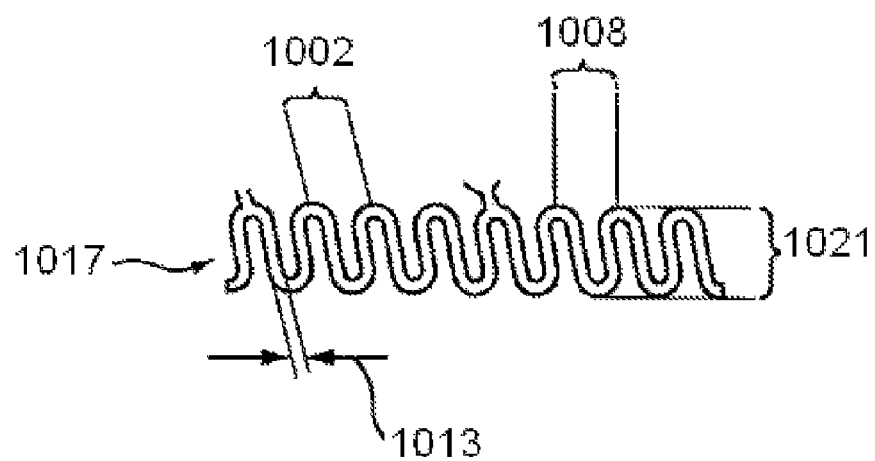
FIG. 16 is a planar view of a flattened portion of part of the endzone shown in FIG. 15.
Figure 17:
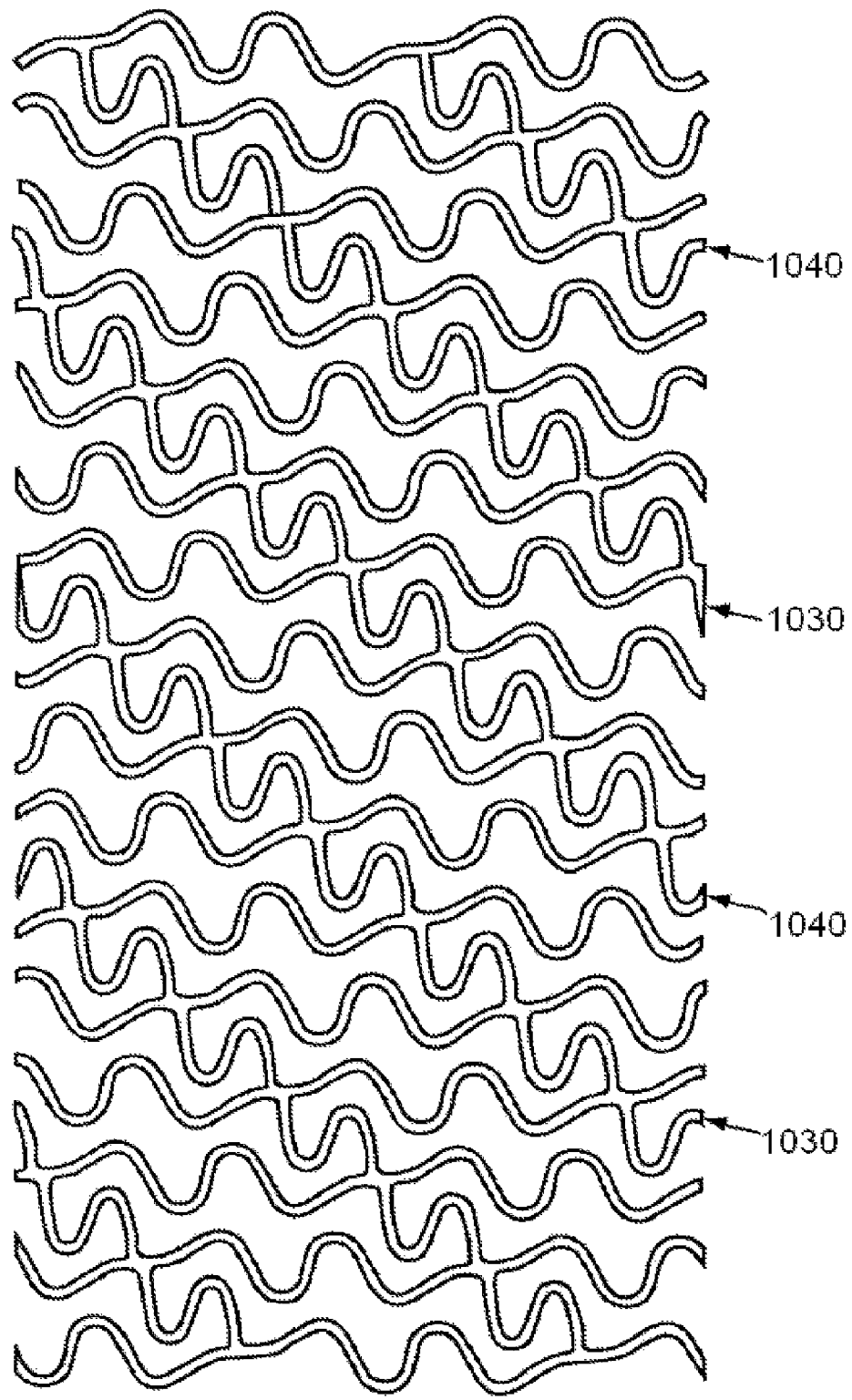
FIG. 17 is a planar view of a flattened portion of an expandable stent according to the present invention, after the stent has been deployed in a lumen.

Some, but not all embodiments, of the present invention may employ endzones 1010 and 1020. (See FIGS. 8, 9, and 18). Stents that employ endzones will generally have two endzone regions straddling a central zone in the middle of the stent. The stents may also have a transition region between the endzone and the central zone. The transition region serves to help smoothly transition between the expanded middle region and portions of the end of the stent that remain unexpanded after the stent is implanted. The size and characteristics of the transition region are a function of the material and geometry of the stent. For example, the transition range properties vary as a function of, among other things, the helical angle of the first helical segments, the number of curved segments located in the endzones, and the angle .epsilon. of the linear portions of the segments forming the endzones. (See e.g. FIG. 15).

The endzones 1010 and 1020 may take numerous forms. In some embodiments, the endzones may be comprised of one or more rings 1017. (See FIG. 15). The rings 1017 may be generally cylindrically shaped, and in some embodiments, right cylindrically shaped. In one embodiment, the rings are formed from linear segments 1028 joined together by curved segments 1029 to form a pattern. The pattern, which is preferably—but not necessarily—a repeating pattern may take numerous forms, including the one shown. The endzones 1010 and 1020 may be comprised of a plurality of rings 1017 attached together. Struts 1015 may be used to attach the rings together to form the endzone and to attach the endzone to the main body 1011. The struts, in some embodiments, act as cantilever springs and there stiffness, which is a function of their width and thickness, may define bending properties of the stent along its cylindrical axis 1005.

In the embodiment shown in FIGS. 8, 14, 15, and 16, which is exemplary only, the linear segments 1028 in the endzone 1010, are oriented at an angle c relative to the cylindrical axis of the stent. In one embodiment, the angle c is greater than 0 degrees. In another embodiment, c may range from 0 to 45 degrees and in still another embodiment is preferably about 10 degrees. The segments of the endzone may have a filament width 1013 of between 0.002 and 0.007 inches. In one embodiment, the repeating pattern of the endzone has a period 1002 of about 0.027 inches and an amplitude 1021 of about 0.043 inches. Other values may be used. As is shown in FIG. 8, the struts 1015, which are but one way to attach the endzones 1010 and 1020 to the main body 1011, may, in one embodiment have a width of between 0.002 inches and 0.08 inches and preferably the width does not exceed the wall thickness, which typically—but not necessarily ranges from about 0.002 to 0.008 inches.

Figure 18:
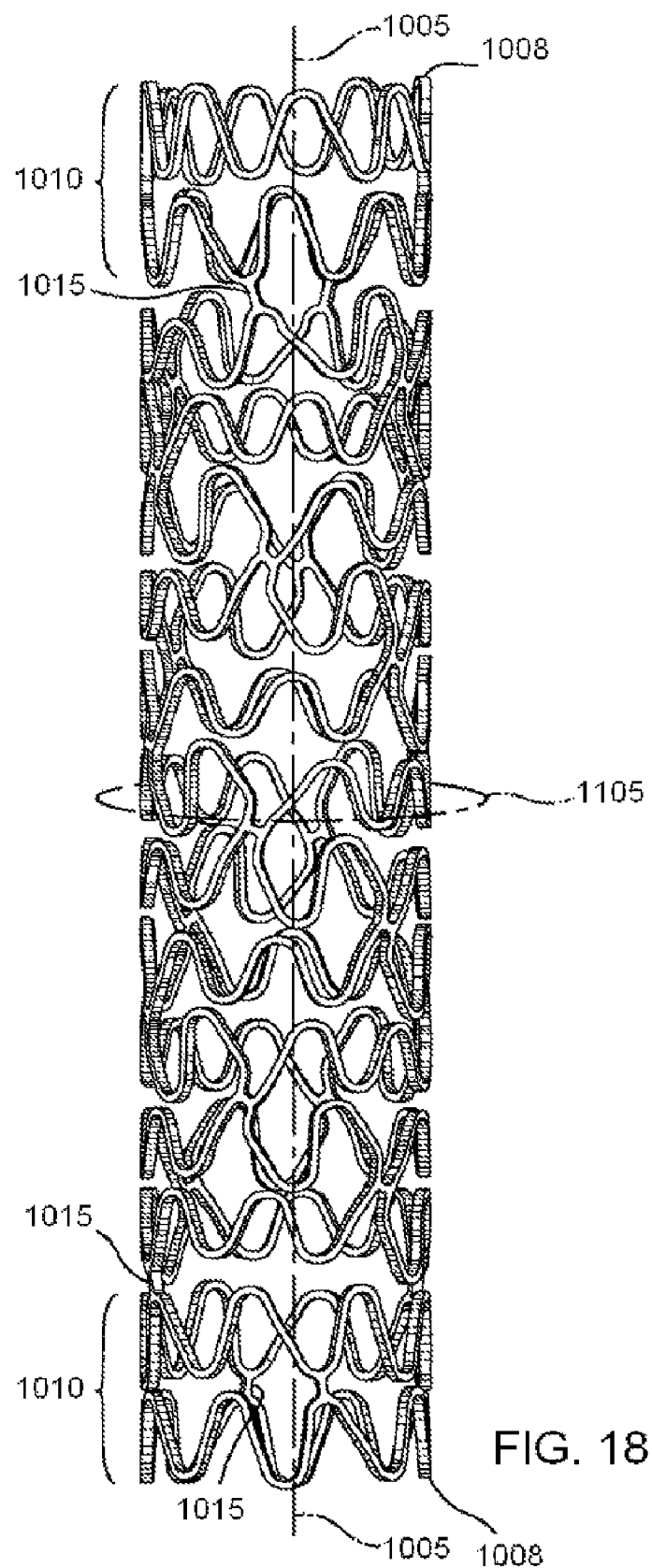
FIG. 18 is three dimensional view of an alternative embodiment of the present invention.
Figure 19:
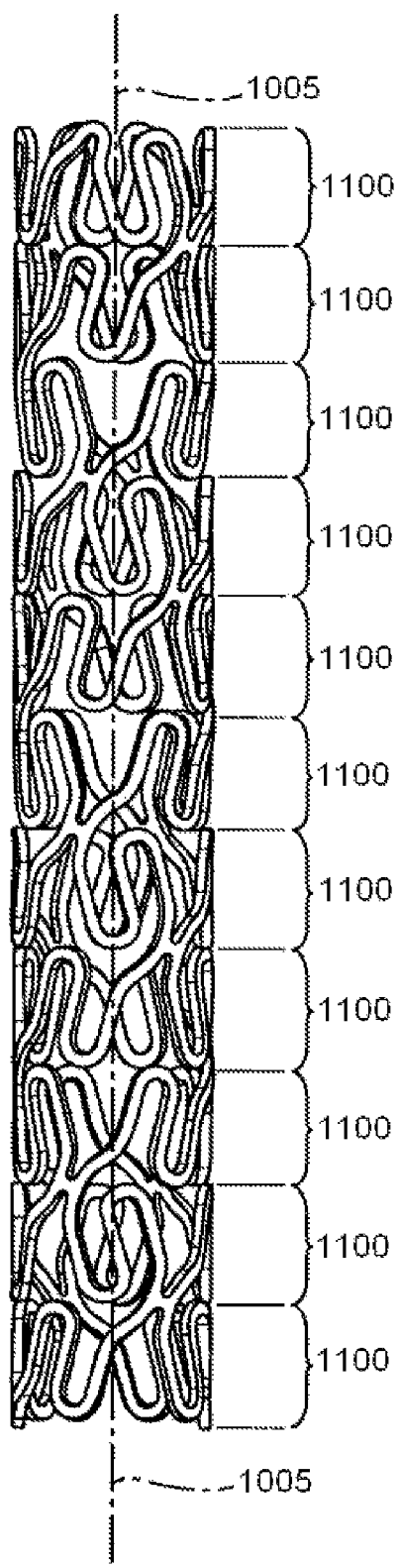
FIG. 19 is a three dimensional view of another stent according to the present invention.
Figure 20:
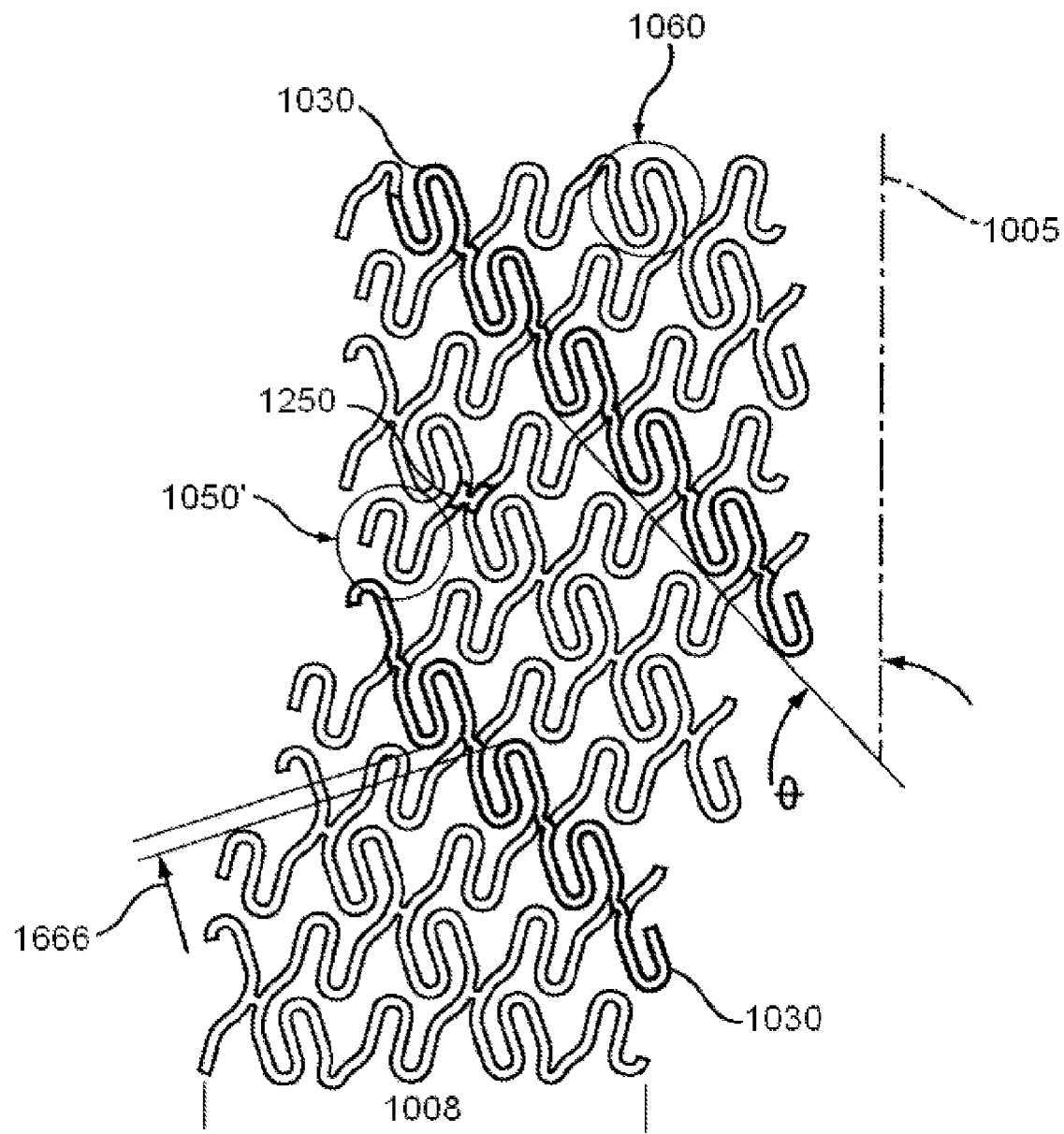
FIG. 20 is a planar view of the stent shown in 19.
Figure 21:
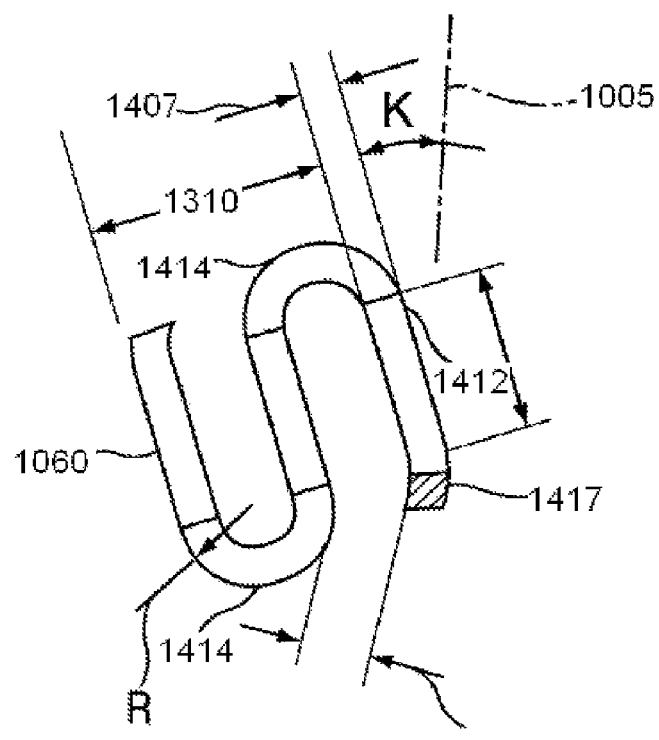
FIG. 21 is a detailed view of a portion of FIG. 20.

The stent of the present invention may, after insertion into a vessel, be expanded such that it plastically deforms from the unexpanded state to an expanded state having a diameter increase of about 400 to 500%, which results in a larger circumference 1105. (See FIG. 18). FIG. 18 depicts the stent shown in FIG. 8 in an expanded state. Upon expansion the stent's outer diameter in one particular embodiment increases from 1.0 mm to 3.00 mm and maintains a stent-to-vessel ratio in the expanded state that is greater than on average 16%.

Figure 22:
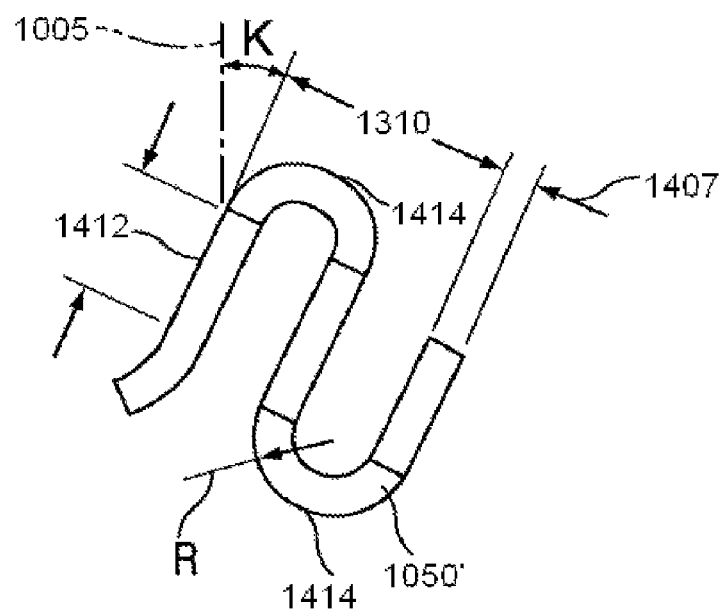
FIG. 22 is a detailed view of another portion of FIG. 20.

While endzones 1010 and 1020 may be used to provide square edge, not all stents according to the present invention require endzones. FIGS. 19-22 depict an endzoneless stent. Like the stent shown in FIG. 8, the stent of FIGS. 19-22 comprises a plurality of adjacent cylindrical elements 1100. The cylindrical elements 1100 are formed from a plurality of first circumferential elements 1050' and second circumferential elements 1060. The first circumferential elements 1050' of the stent in FIGS. 19-22 are substantially identical to the second circumferential element 1060 except that they are rotated to have a different orientation. The circumferential elements may be generally S-shaped having a linear portion 1412, a curved portion 1414 having a radius R, and an angled portion 1417. R may vary widely depending on overall stent characteristics and in one embodiment varies between 0.001 and 0.02 inches and is preferably about 0.0083 inches. The angled portion 1417 is spaced a distance 1499 from the linear portion. In one particular embodiment, the distance 1499 may vary from 0.002 to 0.020 inches and is preferably about 0.007 inches. The filament width 1407 of the elements may, in one embodiment, be about 0.13 mm. The circumferential elements depicted in FIG. 21 and the expansion elements depicted in FIG. 22 are positioned about the cylindrical axis 1005 as defined by angle K and may be generally S-shaped having a linear portion 1412, a curved portion 1414 having a radius R, and an angled portion 1417. The angle K may vary widely depending on overall stent characteristics and range of radial compression or expansion about the axis 5.

Adjacent cylindrical elements 1100 are joined together by connecting first circumferential elements 1050' in each cylindrical element 1100 with first circumferential elements 1050' in an adjacent cylindrical element 1100, such that the first circumferential elements 1050' in adjacent cylindrical elements 1100 form helixes through the stent and such that second circumferential elements form helixes through the stent having an angle θ relative to the axis 1005. In some embodiments, a connecting segment 1250 (see FIG. 14) is used to connect first circumferential elements in adjacent cylindrical elements 1100 and to connect second circumferential elements 1060 in adjacent cylindrical elements 1100. In addition, the connecting segment, connects first circumferential elements 1050' in each cylindrical element 1100 with two second circumferential elements 1060 in each cylindrical element 1100. In one embodiment, the individual cylindrical elements 1100 are adjacent to each other and are located a distance 1666 apart. In one embodiment, the preferred may range between 0.002 and 0.020 inches, and is preferably about 0.009 inches.

The above description of the stent of the present invention is illustrative and not exhaustive. Various modifications may be made to the stent to change its overall characteristics without deviating from the scope and spirit of the invention as defined by the claims. For example and without limitation, the increasing the length of the linear segments and or increasing the arc of the second circumferential elements 1060 will decrease the amount of radial force required to expand each circular section and will increase flexibility. Increasing the angle Ω of the second circumferential element 1060 will: (i) increase the amount of radial force required for expansion, (ii) increase surface area, and (iii) decrease flexibility. Likewise, various modifications may be made to the struts 1015. (See FIG. 9). Increasing strut width and wall thickness will: (i) increase surface area, (ii) increase radial strength, (iii) increase pressure required to expand the stent radially, (iv) decrease flexibility, and, in the case of increased wall thickness, (v) increase radiopacity.

The stent of the present invention may be manufactured in numerous ways. The stent may be formed from a metallic tube by removing various portions of the tube's wall to form the patterns described herein. The resulting stent will thus be formed from a single contiguous piece of material, eliminating the need for connecting various segments together. Material from the tube wall may be removed using various techniques including laser (YAG laser for example), electrical discharge, chemical etching, metal cutting, a combination of these techniques, or other well known techniques. See e.g. U.S. Pat. Nos. 5,879,381 to Moriuchi et al. and 6,117,165 to Becker, which are hereby incorporated in their entirety by reference. Forming stents in this manner allows for creation of a substantially stress-free structure where the helical segments are integral with the circumferential elements. In one embodiment, the tube from which the stent is formed may have an internal diameter of about 3.0 mm, a wall thickness of about 1.0 mm and a length of about 30 mm. Tubes having other dimensions may be used. In particular, the length may be adapted to that of the diseased part of the lumen in which the stent is to be placed. This may avoid using separate stents to cover the total diseased area.

Those skilled in the art will recognize that the stent and manufacturing method described above are illustrative and not exhaustive of the present invention and that modifications and variations may be made without deviating from the scope and spirit of the invention as defined by the following claims.

What is claimed is:

1. A stent comprising:
  a plurality of contiguous filaments arranged to form:
  (i) a plurality of first helical segments, each first helical segment consisting of a plurality of substantially S-curved undulations alternating with a plurality of connection elements, each S-curved undulation defined as a contiguous filament segment extending between two consecutive connection elements, and each connection element including a substantially linear strut angled with respect to a longitudinal axis of the stent; and
  (ii) a second helical segment consisting of a plurality of undulations alternating with a plurality of the connection elements, each undulation defined as a contiguous filament segment extending between two consecutive connection elements and having a circumferential length larger than a circumferential length defined by each substantially S-curved undulation, wherein each undulation consists of five linear segments connected together by curved portions;
  the first and second helical segments having different pitches and crossing each other at the connection elements that are integral portions of the first and second helical segments.

2. The stent of claim 1, wherein each of the substantially S-curved undulations includes a plurality of linear filament segments that are substantially parallel to a longitudinal axis of the stent.

3. A stent having an a generally cylindrical shaped body, comprising:
  a first repetitious pattern of contiguous filament segments consisting of a plurality of substantially S-shaped undulations alternating with a plurality of connection elements propagating generally helically through the body, the first repetitious pattern having a first pitch and each S-shaped undulation defined as a contiguous filament segment spanning between two consecutive connection elements; and
  a second repetitious pattern consisting of the connection elements alternating with a plurality of undulations, each undulation spanning between two consecutive connection elements and defining a length greater than a length of each substantially S-shaped undulation, wherein each undulation cosists of five linear segmens connected together by curved portions, and wherein the second repetitious pattern propagates helically through the body and has a second pitch that is different than the first pitch.

4. The stent of claim 3, wherein each of the substantially S-shaped undulations includes a plurality of linear filament segments that are substantially parallel to a longitudinal axis of the stent.

5. The stent of claim 3, wherein the connection element includes a substantially linear strut angled with respect to a longitudinal axis of the stent.

6. A stent comprising:
  a plurality of filament segments arranged to form a plurality of first repetitious patterns, eacg first repetitious pattern consisting of substantially S-shaped segments and connection elements advancing substantially helically along a longitudinal axis of the stent, wherein each S-shaped segment is connected to exactly two connection elements, and each connection element includes a substantially linear strut angled with respect to a longitudinal axis of the stent;
  wherein the connection elements are staggered to form a second repetitious helical pattern with a plurality of undulations, each undulation having a longer length than a length of each of the substantially S-shaped segments, and wherein each undulation is connected to exactly two connection elements.

7. The stent of claim 6, wherein at least a portion of the first repetitious pattern is generally sinusoidal.

8. The stent of claim 6, wherein the connection elements forming the second pattern are not contiguous.

9. The stent of claim 6, wherein the first and second repetitious helical patterns have opposing pitches.

10. The stent of claim 9, wherein the first and second repetitious helical patterns share common filament segments.

11. The stent of claim 6, wherein each of the substantially S-shaped segments includes a plurality of linear filament segments that are substantially parallel to the longitudinal axis of the stent.

* * * * *